United States Patent
Makino et al.

(10) Patent No.: US 12,042,325 B2
(45) Date of Patent: Jul. 23, 2024

(54) MEDICAL IMAGE PROCESSING APPARATUS

(71) Applicant: FUJIFILM CORPORATION, Tokyo (JP)

(72) Inventors: Kazuhiro Makino, Kanagawa (JP); Akihito Bettoyashiki, Kanagawa (JP); Koji Taninai, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 287 days.

(21) Appl. No.: 17/748,043

(22) Filed: May 19, 2022

(65) Prior Publication Data
US 2022/0378392 A1 Dec. 1, 2022

(30) Foreign Application Priority Data
May 26, 2021 (JP) .................................. 2021-088624

(51) Int. Cl.
*A61B 6/00* (2024.01)

(52) U.S. Cl.
CPC .............. *A61B 6/56* (2013.01); *A61B 6/4405* (2013.01); *A61B 6/5211* (2013.01); *A61B 6/54* (2013.01)

(58) Field of Classification Search
CPC ........... A61B 6/54; A61B 6/56; A61B 6/4405; A61B 6/5211
See application file for complete search history.

(56) References Cited

U.S. PATENT DOCUMENTS

| | | | | |
|---|---|---|---|---|
| 2006/0054829 | A1* | 3/2006 | Tsuchino | A61B 6/4488 250/370.09 |
| 2006/0215807 | A1* | 9/2006 | Ohara | G03B 42/02 378/11 |
| 2012/0076274 | A1* | 3/2012 | Shimizukawa | A61B 6/4283 378/98.5 |
| 2012/0161026 | A1* | 6/2012 | Kitano | A61B 6/4405 250/394 |
| 2012/0300413 | A1* | 11/2012 | Iida | A61B 6/548 361/728 |
| 2014/0124678 | A1* | 5/2014 | Yoneyama | H04N 25/75 250/393 |
| 2015/0071414 | A1* | 3/2015 | Oda | A61B 6/54 378/207 |
| 2015/0168566 | A1* | 6/2015 | Shikino | H04N 5/32 250/394 |
| 2016/0345920 | A1* | 12/2016 | Tajima | A61B 6/563 |
| 2019/0046134 | A1* | 2/2019 | Imamura | A61B 6/465 |
| 2020/0015770 | A1* | 1/2020 | Oda | A61B 6/54 |
| 2021/0038182 | A1* | 2/2021 | Nishijima | A61B 6/54 |

FOREIGN PATENT DOCUMENTS

| | | |
|---|---|---|
| JP | 2004-173906 A | 6/2004 |
| JP | 2005-27739 A | 2/2005 |

* cited by examiner

*Primary Examiner* — Blake C Riddick
(74) *Attorney, Agent, or Firm* — SOLARIS Intellectual Property Group, PLLC

(57) ABSTRACT

The medical image processing apparatus includes a first processor, a second processor that executes image processing on a medical image in response to an instruction from the first processor, and a battery that supplies power to the first processor and the second processor. The second processor executes the image processing with a selected processing method among a plurality of processing methods that are different in amount of power consumption.

12 Claims, 14 Drawing Sheets

| BATTERY RESIDUAL QUANTITY | PROCESSING METHOD |
|---|---|
| TO 30% | FIRST DETECTION MODEL |
| 30 TO 60% | SECOND DETECTION MODEL |
| 60 TO 100% | THIRD DETECTION MODEL |

| PURPOSE OF CAD PROCESSING | PROCESSING METHOD |
|---|---|
| PROGRESS OBSERVATION | FIRST DETECTION MODEL |
| PRECISE DIAGNOSIS | SECOND DETECTION MODEL |
| CAUSE ANALYSIS | THIRD DETECTION MODEL |

| PURPOSE OF CAD PROCESSING | BATTERY RESIDUAL QUANTITY | PROCESSING METHOD |
|---|---|---|
| PROGRESS OBSERVATION | TO 30% | FIRST DETECTION MODEL |
| | 30 TO 60% | FIRST DETECTION MODEL |
| | 60 TO 100% | SECOND DETECTION MODEL |
| PRECISE DIAGNOSIS | TO 30% | SECOND DETECTION MODEL |
| | 30 TO 60% | SECOND DETECTION MODEL |
| | 60 TO 100% | SECOND DETECTION MODEL |
| CAUSE ANALYSIS | TO 30% | SECOND DETECTION MODEL |
| | 30 TO 60% | THIRD DETECTION MODEL |
| | 60 TO 100% | THIRD DETECTION MODEL |

| ORDER No. | PATIENT ID | IMAGING PROCEDURE | MEDICAL EXAMINATION PURPOSE |
|---|---|---|---|
| 1 | A0001 | ABDOMEN/UPRIGHT/FRONT | PRECISE DIAGNOSIS |
| 2 | A0002 | CHEST/DECUBITUS/FRONT | CAUSE ANALYSIS |
| 3 | A0003 | KNEE/BENDING/SIDE | PROGRESS OBSERVATION |
| ⋮ | ⋮ | ⋮ | ⋮ |

400

| BATTERY RESIDUAL QUANTITY | PROCESSING METHOD | |
|---|---|---|
| | DIAGNOSIS SUPPORT UNIT FOR USE | DETECTION MODEL FOR USE |
| TO 10% | SECOND DIAGNOSIS SUPPORT UNIT | FOURTH DETECTION MODEL |
| 10 TO 30% | FIRST DIAGNOSIS SUPPORT UNIT | FIRST DETECTION MODEL |
| 30 TO 60% | SECOND DIAGNOSIS SUPPORT UNIT | SECOND DETECTION MODEL |
| 60 TO 100% | THIRD DIAGNOSIS SUPPORT UNIT | THIRD DETECTION MODEL |

FIG. 20
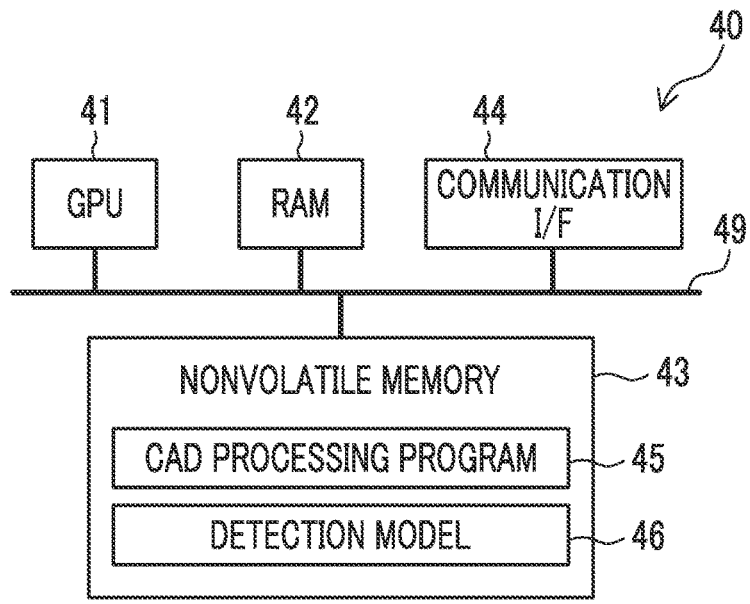
FIG. 21
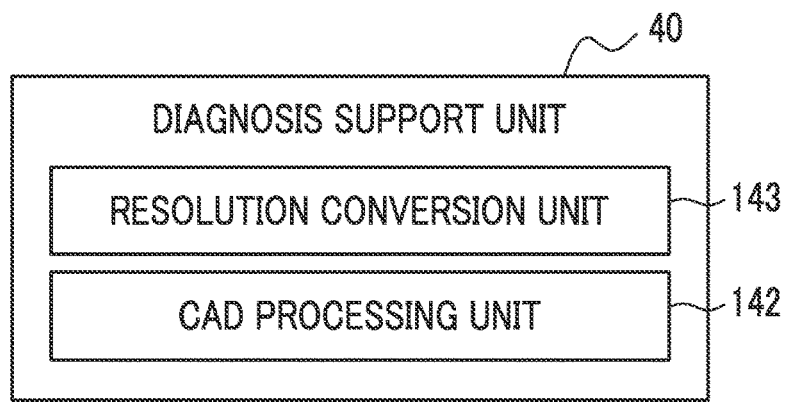
FIG. 22
| BATTERY RESIDUAL QUANTITY | PROCESSING METHOD |
|---|---|
| TO 30% | LOW RESOLUTION |
| 30 TO 60% | MIDDLE RESOLUTION |
| 60 TO 100% | HIGH RESOLUTION |

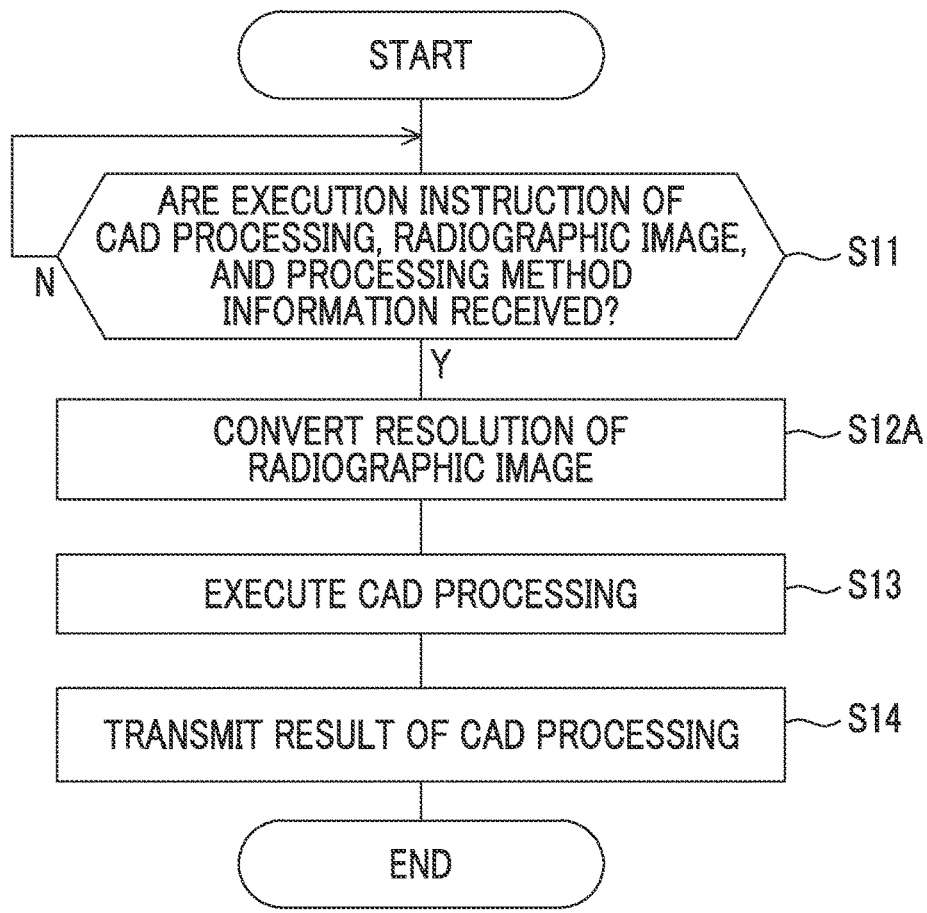
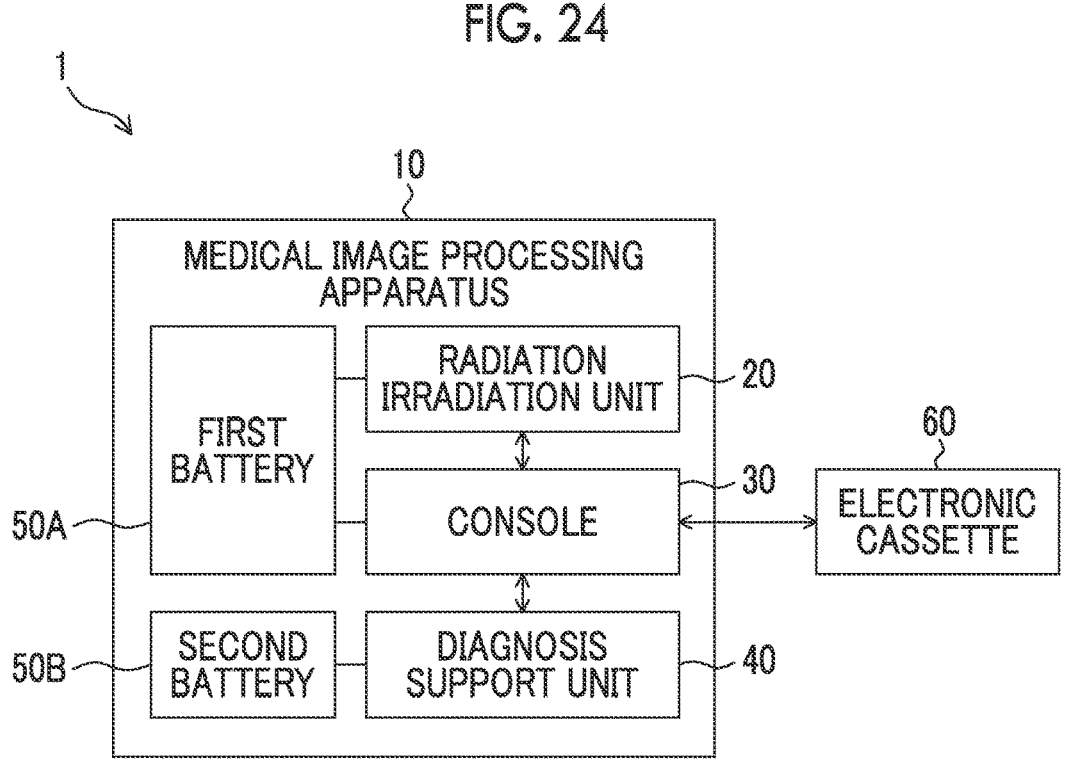

MEDICAL IMAGE PROCESSING APPARATUS

CROSS-REFERENCE TO RELATED APPLICATIONS

The present application claims priority under 35 U.S.C. § 119 to Japanese Patent Application No. 2021-088624, filed on May 26, 2021. The above application is hereby expressly incorporated by reference, in its entirety, into the present application.

BACKGROUND

1. Technical Field

A technique of the disclosure relates to a medical image processing apparatus.

2. Description of the Related Art

As a technique regarding a medical image processing apparatus that is driven with a battery, among medical image processing apparatuses that process a medical image, such as a radiographic image, the following technique is known. For example, JP2004-173906A describes an X-ray examination apparatus that switches between processing of storing, in a storage medium, an image obtained by subjecting a captured image to image processing for diagnosis along with image correction processing at the time of image capturing in a storage medium and processing of storing, in the storage medium, an image subjected to only the image correction processing. The X-ray examination apparatus performs the switching in a case where a residual quantity of an internal power supply is smaller than a capacity set in advance.

JP2005-27739A describes an X-ray image capturing apparatus including a planar sensor panel that captures an X-ray image, a controller that stores the captured image or executes image processing, and a battery that drives the units. In a case where an AC power supply is not supplied, only the storage of the image acquired from the planar sensor panel is performed, and the image processing is not executed.

SUMMARY

There is known a medical image processing apparatus that provides information useful for diagnosis, such as detecting and presenting a lesion from a medical image, by executing image processing of analyzing a medical image, such as a radiographic image, using a computer. Diagnosis support accompanied with the image processing using the computer is referred to as computer aided diagnosis (CAD). The CAD processing is accompanied with the image processing on the medical image. Thus, in a case where a processor specialized for image processing, such as a graphics processing unit (GPU), is made to execute the CAD processing, it is possible to considerably reduce a processing time compared to a case where a central processing unit (CPU) that is good at general-purpose processing.

On the other hand, it has been suggested that a CAD function is implemented in a mobile radiography apparatus (so-called treatment cart) comprising an irradiation unit that performs irradiation of radiation, a console, and a battery. The CAD function that is implemented in the mobile radiography apparatus is realized by the GPU independent of the console, whereby it is possible to promptly perform diagnosis support with the CAD function at a destination. Note that, in this case, power supply from the battery to the GPU is required, and an amount of power to be consumed from the battery increases. As a result, it is expected that an operation time of the apparatus is shortened or a charging frequency of the battery increases, and efficient rounds may be obstructed.

The technique of the disclosure has been accomplished in view of the above-described points, and an object of the technique of the disclosure is to provide a medical image processing apparatus comprising a processor that executes image processing on a medical image and a battery that supplies power to the processor, having an advantage of suppressing an amount of power to be consumed from the battery.

A medical image processing apparatus according to the technique of the disclosure comprises a first processor, a second processor that executes image processing on a medical image in response to an instruction from the first processor, and a battery that supplies power to the first processor and the second processor. The second processor executes the image processing with a selected processing method among a plurality of processing methods that are different in amount of power consumption.

The first processor may select any one of the plurality of processing methods based on a residual quantity of the battery. The first processor may select any one of the plurality of processing methods based on information indicating a purpose of the image processing. The first processor may select any one of the plurality of processing methods based on information indicating an execution schedule of the image processing.

The plurality of processing methods may be different in calculation processing amount. The plurality of processing methods may be different in the number of pixels of a medical image to be processed.

In a case where a third processor that receives supply of power from a power supply different from the battery to execute image processing is available, the first processor may select any one of the plurality of processing methods of the second processor or a processing method of the third processor. The first processor may select the processing method of the third processor in a case where a residual quantity of the battery is equal to or less than a threshold value.

The medical image may be a radiographic image. In this case, the medical image processing apparatus may further comprise a radiation irradiation unit that receives the supply of power from the battery to perform irradiation of radiation for capturing the radiographic image. The second processor may output information for supporting diagnosis using the medical image through the image processing. In the medical image processing apparatus, a first battery that supplies power to the first processor and a second battery that supplies power to the second processor may be provided. The medical image processing apparatus may be a mobile type.

According to the technique of the disclosure, it is possible to provide a medical image processing apparatus comprising a processor that executes image processing on a medical image and a battery that supplies power to the processor, having an advantage capable of suppressing an amount of power to be consumed from the battery.

BRIEF DESCRIPTION OF THE DRAWINGS

Exemplary embodiments according to the technique of the present disclosure will be described in detail based on the following figures, wherein:

FIG. 13 is a diagram showing an example of a processing method selection table according to another embodiment of the technique of the disclosure;

FIG. 14 is a diagram showing an example of a processing method selection table according to another embodiment of the technique of the disclosure;

FIG. 20 is a diagram showing an example of the hardware configuration of a diagnosis support unit according to another embodiment of the technique of the disclosure;

FIG. 21 is a functional block diagram showing an example of the functional configuration of the diagnosis support unit according to another embodiment of the technique of the disclosure;

FIG. 22 is a diagram showing an example of a processing method selection table according to another embodiment of the technique of the disclosure;

FIG. 23 is a flowchart illustrating an example of a flow of processing that is executed by executing a CAD processing program according to another embodiment of the technique of the disclosure; and FIG. 24 is a block diagram showing an example of the configuration of a medical image processing apparatus according to another embodiment of the technique of the disclosure.

DETAILED DESCRIPTION

Figure 1:
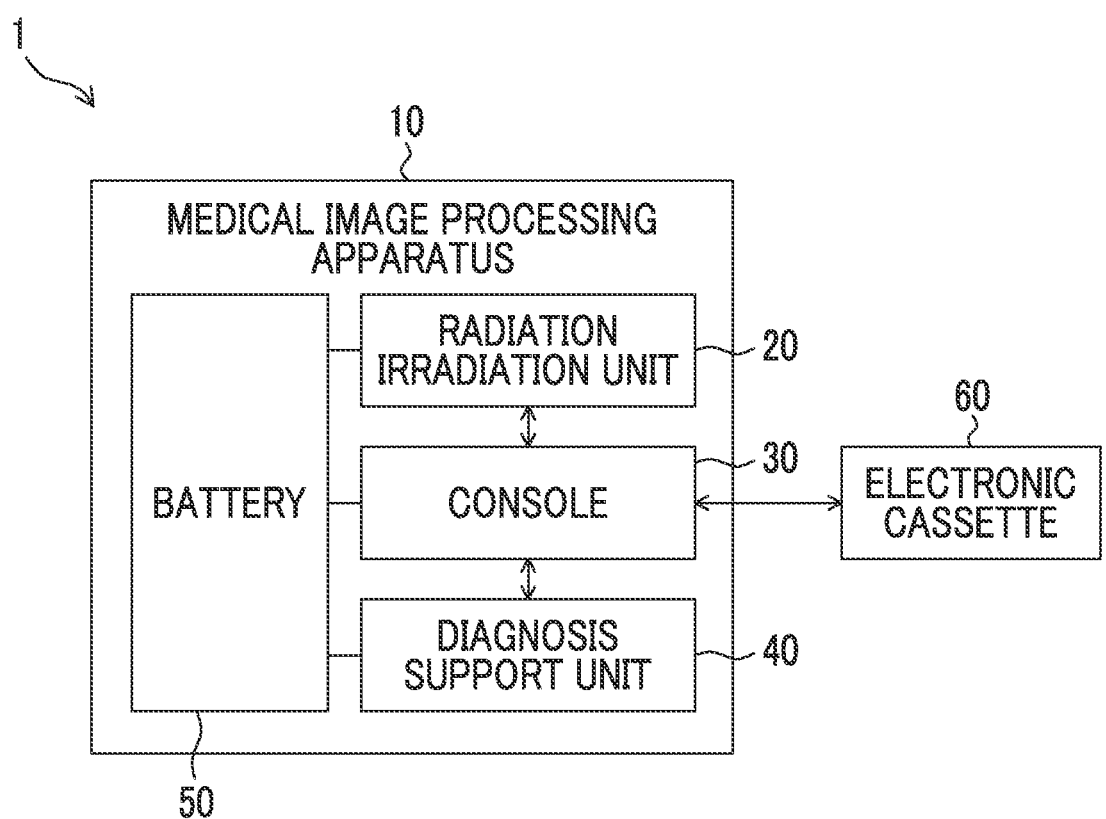
FIG. 1 is a block diagram showing an example of the configuration of a medical examination system according to an embodiment of the technique of the disclosure.

Hereinafter, an example of an embodiment of the technique of the disclosure will be described referring to the drawings. In the drawings, the same or equivalent components are represented by the same reference numerals, and overlapping description will not be repeated.

First Embodiment

Figure 2:
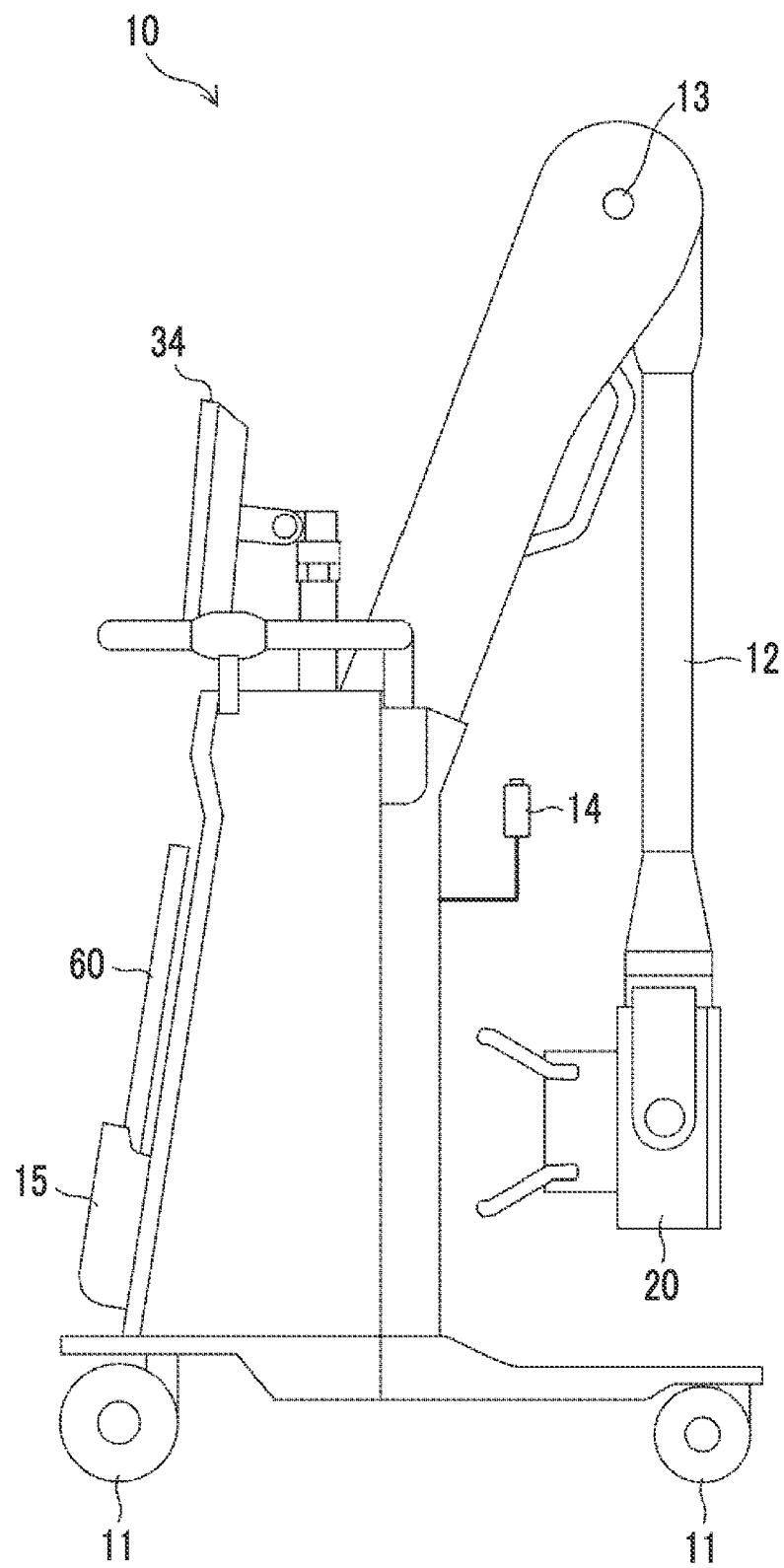
FIG. 2 is a side view showing an example of the appearance of the medical image processing apparatus according to the embodiment of the technique of the disclosure.

FIG. 1 is a diagram showing an example of the configuration of a medical examination system 1 according to an embodiment of the technique of the disclosure. The medical examination system 1 includes a medical image processing apparatus 10 and an electronic cassette 60. FIG. 2 is a side view showing an example of the appearance of the medical image processing apparatus 10. The medical image processing apparatus 10 has a function of acquiring a radiographic image that is obtained by irradiating a patient as a subject with radiation, such as X-rays, executing CAD processing accompanied with image processing on the radiographic image, and presenting a result of the CAD processing. The radiographic image is an example of a "medical image" in the technique of the disclosure and is generated by an electronic cassette 60.

As shown in FIG. 2, the medical image processing apparatus 10 has wheels 11 in a bottom portion. That is, the medical image processing apparatus 10 is a portable mobile type. Accordingly, the medical image processing apparatus 10 can be used for rounds in which a physician goes round and examines inpatients in a hospital ward. As shown in FIG. 1, the medical image processing apparatus 10 comprises a radiation irradiation unit 20, a console 30, a diagnosis support unit 40, and a battery 50.

The radiation irradiation unit 20 has a function of performing irradiation of radiation, such as X-rays, with which the subject is irradiated, in a case of capturing a radiographic image. The radiation irradiation unit 20 is provided at a distal end of an arm part 12. The arm part 12 can expand and contract in a longitudinal direction and can rotate with a shaft part 13 as a rotation axis.

The console 30 and the diagnosis support unit 40 include computers independent of each other. The battery 50 supplies power to each of the radiation irradiation unit 20, the console 30, and the diagnosis support unit 40. The battery 50 is a secondary battery, such as a lithium polymer battery and can be charged through a connector (not shown). The battery 50 has a function of measuring a residual quantity and notifying the console 30 of the residual quantity. The console 30, the diagnosis support unit 40, and the battery 50 are incorporated in the medical image processing apparatus 10.

Figure 3:
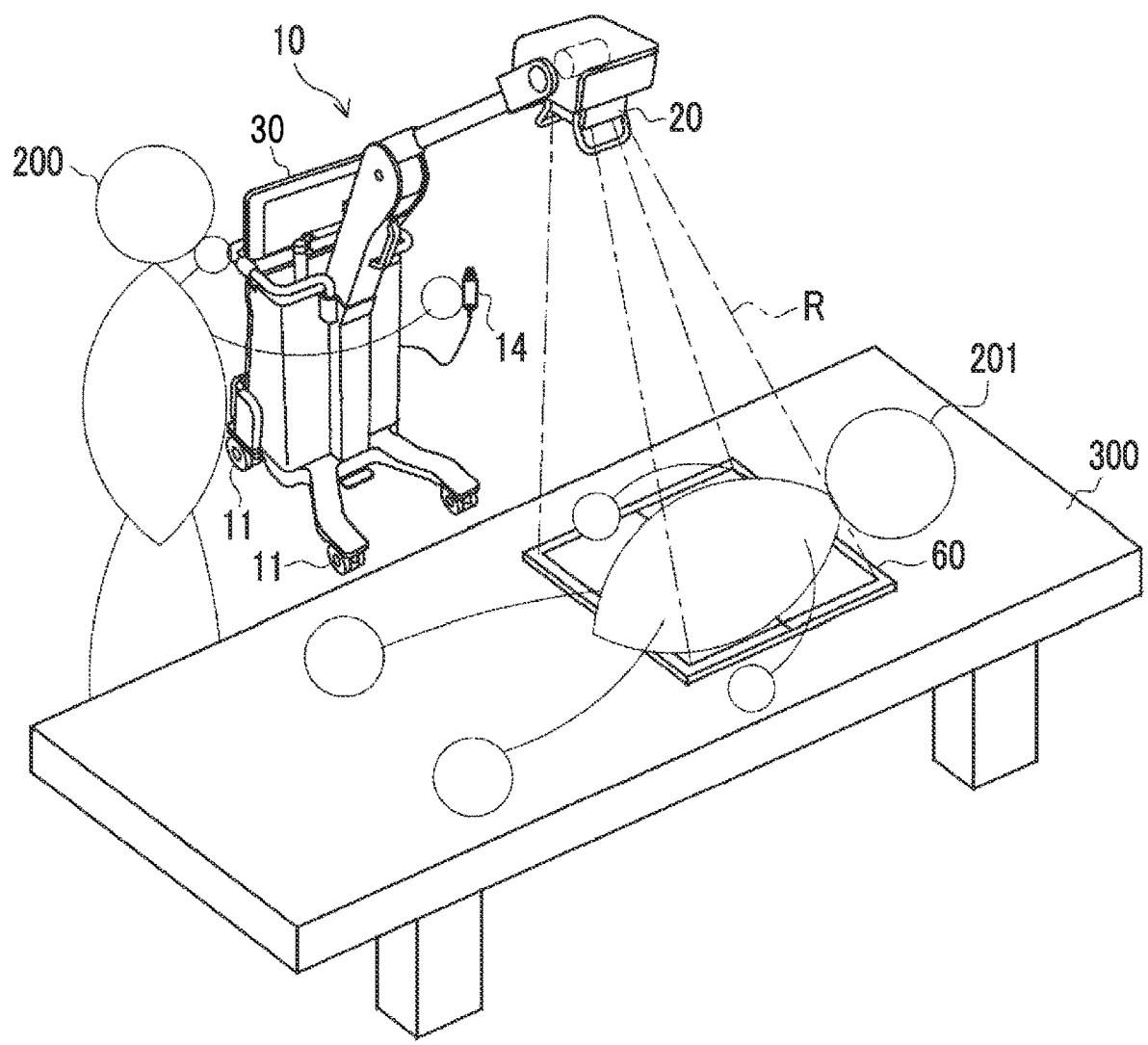
FIG. 3 is a perspective view showing an example of a capturing method of a radiographic image.

FIG. 3 is a perspective view showing an example of a method of capturing a radiographic image using the medical image processing apparatus 10 and the electronic cassette 60. FIG. 3 illustrates a case of capturing a radiographic image of a chest of a subject 201 in a supine state on an examination table 300. The electronic cassette 60 is disposed at a position facing the radiation irradiation unit 20. The subject 201 is disposed between the radiation irradiation unit 20 and the electronic cassette 60 such that an imaging target part falls within an irradiation field of radiation.

A user 200, such as a radiology technician or a physician, operates an irradiation switch 14, whereby irradiation of radiation R is performed from the radiation irradiation unit 20. The radiation transmitted through the subject 201 reaches the electronic cassette 60. The electronic cassette 60 is a known portable flat panel detector (FPD) that detects the radiation transmitted through the subject 201 to generate a radiographic image. The electronic cassette 60 has a function of automatically detecting an irradiation start of the radiation R from the radiation irradiation unit 20. For this reason, the electronic cassette 60 can generate a radiographic image without being connected to the medical image processing apparatus 10. The electronic cassette 60 has a wireless communication function and transmits the generated radiographic image to the console 30 through wireless communication. The medical image processing apparatus 10 has a housing portion 15 (see FIG. 2) that houses the electronic cassette 60. In a state in which the electronic cassette 60 is housed in the housing portion 15, a battery (not shown) incorporated in the electronic cassette 60 can be charged.

Hereinafter, each constituent element of the medical image processing apparatus 10 shown in FIG. 1 will be described in detail.

Figure 4:
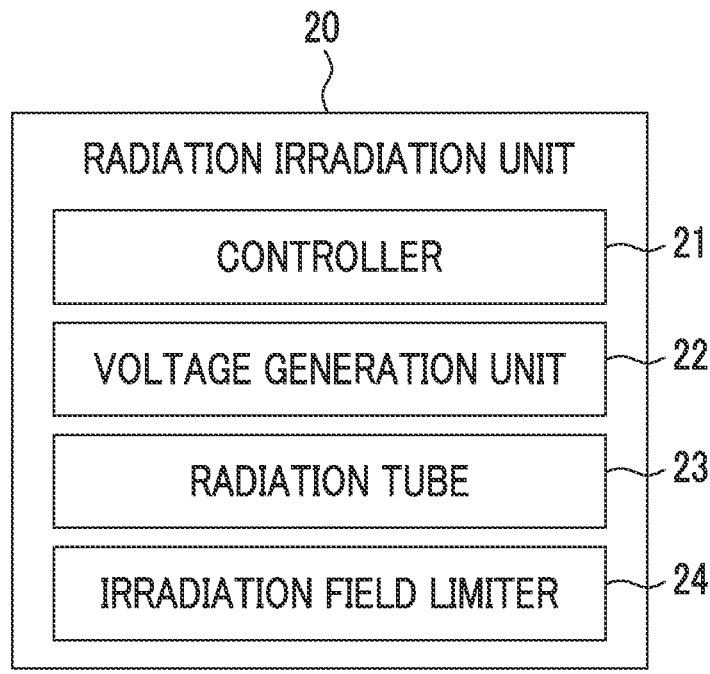
FIG. 4 is a block diagram showing an example of the configuration of a radiation irradiation unit according to the embodiment of the technique of the disclosure.

FIG. 4 is a block diagram showing an example of the configuration of the radiation irradiation unit 20. The radiation irradiation unit 20 comprises a controller 21, a voltage generation unit 22, a radiation tube 23, and an irradiation field limiter 24. The radiation tube 23 includes a filament, a target, and a grid electrode (all are not shown). A voltage that is output from the voltage generation unit 22 is applied across the filament as a cathode and the target as an anode. The voltage that is applied across the filament and the target is referred to as a tube voltage. The filament emits thermoelectrons depending on the applied tube voltage toward the target. The target emits radiation with collision of thermoelectrons from the filament. The grid electrode is disposed between the filament and the target. The grid electrode controls a flow rate of the thermoelectrons from the filament toward the target. The flow rate of the thermoelectrons from the filament toward the target is referred to as a tube current. The controller 21 controls the tube voltage, the tube current, and an irradiation time of radiation based on an instruction from the console 30.

The irradiation switch 14 is a two-stage push type switch that is provided for the user, such as a radiology technician or a physician, to give an instruction to start the irradiation of the radiation. In a case where the irradiation switch 14 is pushed to a first stage, the filament is warmed up, and the rotation of the target is started. When the filament reaches a prescribed temperature, and the target reaches a prescribed rotation speed, warm-up is completed. In a state in which warm-up is completed, in a case where the irradiation switch 14 is pushed to a second stage, the voltage is applied from the voltage generation unit 22, and radiation is emitted from the radiation tube 23.

The irradiation field limiter 24 limits an irradiation field of the radiation emitted from the radiation tube 23. The irradiation field limiter 24 has, for example, a configuration in which four shield plates that shield the radiation are disposed on respective sides of a quadrangle, and an opening of the quadrangle that transmits the radiation is formed in a center portion. The irradiation field limiter 24 changes the positions of the four shield plates to change the size of the opening, and accordingly, changes the size of the irradiation field of the radiation.

Figure 5:
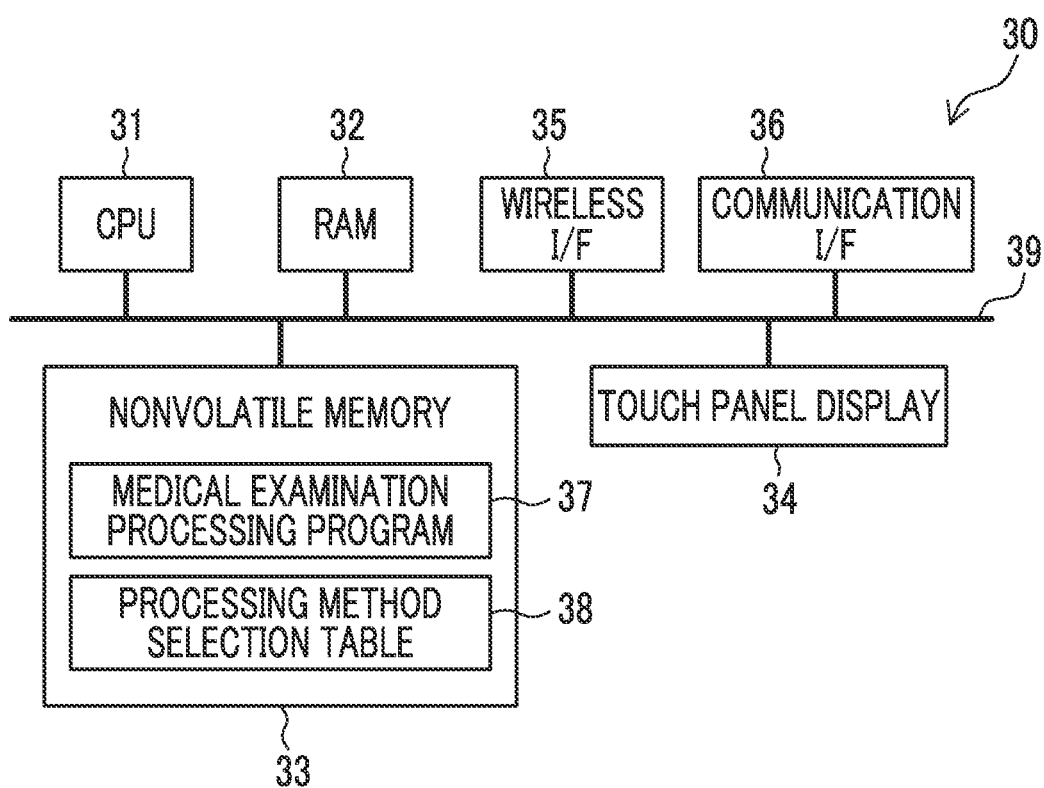
FIG. 5 is a diagram showing an example of the hardware configuration of a console according to the embodiment of the technique of the disclosure.

The console 30 is a computer that integrally controls various kinds of processing to be executed in the medical image processing apparatus 10. FIG. 5 is a diagram showing an example of the hardware configuration of the console 30. The console 30 has a CPU 31, a random access memory (RAM) 32, a nonvolatile memory 33, a touch panel display 34, a wireless interface 35, and a communication interface 36. The CPU 31, the RAM 32, the nonvolatile memory 33, the touch panel display 34, the wireless interface 35, and the communication interface 36 are connected to a bus 39.

The nonvolatile memory 33 is a storage device, such as a flash memory, and stores a medical examination processing program 37 and a processing method selection table 38 described below. The RAM 32 is a work memory on which the CPU 31 executes processing. The CPU 31 loads the medical examination processing program 37 stored in the nonvolatile memory 33 to the RAM 32 and executes processing depending on the medical examination processing program 37. The CPU 31 is an example of a "first processor" in the technique of the disclosure.

The touch panel display 34 functions as an input device that receives an input of information for processing to be executed by the CPU 31 and an output device that outputs a result of processing executed by the CPU 31. The input device may include known input means, such as operation buttons, a hardware keyboard, a mouse, and a track ball.

The wireless interface 35 is an interface that is provided for the console 30 to perform transmission and reception of information or data through wireless communication with the electronic cassette 60 and other equipment. The console 30 acquires a radiographic image that is transmitted from the electronic cassette 60 through wireless communication, through the wireless interface 35. The acquired radiographic image is stored in the nonvolatile memory 33.

The communication interface 36 is an interface that is provided for the console 30 to perform transmission and reception of information or data with the diagnosis support unit 40 and other equipment. The communication interface 36 may be, for example, a communication interface conforming to a universal serial bus (USB). The console 30 acquires information indicating a residual quantity of the battery 50 from the battery 50 through the communication interface 36.

The diagnosis support unit 40 is a computer that executes CAD processing accompanied with image processing on a radiographic image in response to an instruction from the console 30. The diagnosis support unit 40 outputs information for supporting diagnosis using a medical image as a result of the CAD processing. The diagnosis support unit 40 detects an abnormal shadow, such as a lesion part, included in the radiographic image as the CAD processing and transmits a result of the detection to the console 30. The diagnosis support unit 40 is configured of a computer independent of the console 30.

Figure 6:
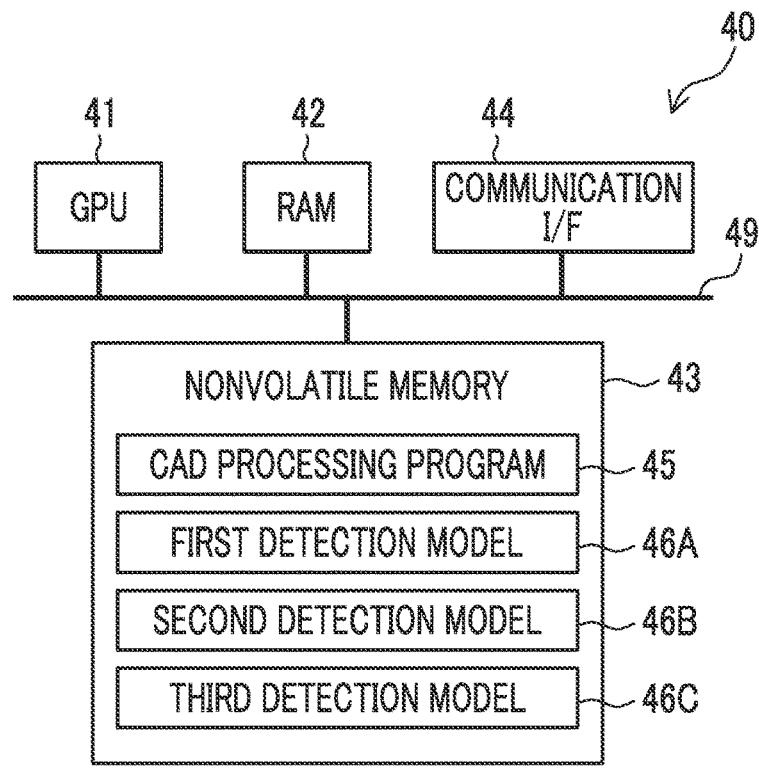
FIG. 6 is a diagram showing an example of the hardware configuration of a diagnosis support unit according to the embodiment of the technique of the disclosure.

FIG. 6 is a diagram showing an example of the hardware configuration of the diagnosis support unit 40. The diagnosis support unit 40 has a graphic processing unit (GPU) 41, a RAM 42, a nonvolatile memory 43, and a communication interface 44. The GPU 41, the RAM 42, the nonvolatile memory 43, and the communication interface 44 are connected to a bus 49.

The GPU 41 is a processor that has a greater number of cores than the CPU 31 in the console 30 and can perform comparatively simple calculations, such as matrix operations, in parallel. For this reason, the GPU 41 can perform the CAD processing accompanied with the image processing of the radiographic image at a higher speed that the CPU 31. The GPU 41 is an example of a "second processor" in the technique of the disclosure.

The nonvolatile memory 43 is a storage device, such as a flash memory, and stores a CAD processing program 45, a first detection model 46A, a second detection model 46B, and a third detection model 46C described below. The RAM 42 is a work memory on which the GPU 41 executes processing. The GPU 41 loads the CAD processing program 45 stored in the nonvolatile memory 43 to the RAM 42 and executes the CAD processing depending on the CAD processing program 45. The communication interface 44 is an interface that is provided for performing transmission and reception of information or data with the console 30 and other equipment. The communication interface 44 may be, for example, a communication interface conforming to a USB.

The diagnosis support unit 40 may have an attachable and detachable form of a so-called "external GPU box" comprising a housing that houses the GPU 41, the RAM 42, the nonvolatile memory 43, and the communication interface 44. The diagnosis support unit 40 may further comprise a CPU for general-purpose processing, in addition to the GPU 41. In this case, it is preferable that the GPU 41 professionally executes the image processing of the radiographic image, and the CPU executes general-purpose processing, such as execution control of a program and communication control with the console 30.

Each of the first to third detection models 46A to 46C is a mathematical model that detects an abnormal shadow, such as a lesion part, included in the radiographic image and is a learned model that performs learning through machine learning. The first to third detection models 46A to 46C are configured using, for example, a neural network. The first to third detection models 46A to 46C are configured using, for example, a deep neural network (DNN) that is a multilayered neural network to be a target of deep learning. As the DNN, for example, a convolutional neural network (CNN) suitable for an image is used.

As the radiographic image as a CAD processing target is input to the first to third detection models 46A to 46C, a detection result of an abnormal shadow, such as a lesion part, included in the radiographic image as a CAD processing target is output from the first to third detection models 46A to 46C. The GPU 41 executes the CAD processing selectively using the first to third detection models 46A to 46C.

The first to third detection models 46A to 46C are different in amount of power consumption in the GPU 41 in a case of detecting an abnormal shadow using the detection model. In the embodiment, the amount of power consumption in a case of using the first detection model 46A is the smallest, and the amount of power consumption in a case of using the third detection model 46C is the greatest. The amount of power consumption in a case of using the second detection model 46B is greater than the amount of power consumption in a case of using the first detection model 46A and smaller than the amount of power consumption in a case of using the third detection model 46C.

In the embodiment, the first to third detection models 46A to 46C are different in calculation processing amount in a case of detecting an abnormal shadow using the detection model. The calculation processing amount in a case of using the first detection model 46A is the smallest, the calculation processing amount in a case of using the third detection model 46C is the greatest, and the calculation processing amount in a case of using the second detection model 46B is greater than the calculation processing amount in a case of using the first detection model 46A and smaller than the calculation processing amount in a case of using the third detection model 46C. For example, the first to third detection models 46A to 46C may be different in the number of intermediate layers of the neural network that configures the detection model. That is, the number of intermediate layers of the first detection model 46A may be the smallest, the number of intermediate layers of the third detection model 46C may be the greatest, and the number of intermediate layers of the second detection model 46B may be greater than the number of intermediate layers of the first detection model 46A and may be smaller than the number of intermediate layers of the third detection model 46C. Accordingly, the detection accuracy of an abnormal shadow in a case of using the first detection model 46A may be the lowest, the detection accuracy of an abnormal shadow in a case of using the third detection model 46C is the highest, and the detection accuracy of an abnormal shadow in a case of using the second detection model 46B may be higher than the detection accuracy of an abnormal shadow in a case of using the first detection model 46A and may be lower than the detection accuracy of an abnormal shadow in a case of using the third detection model 46C.

Figure 7:
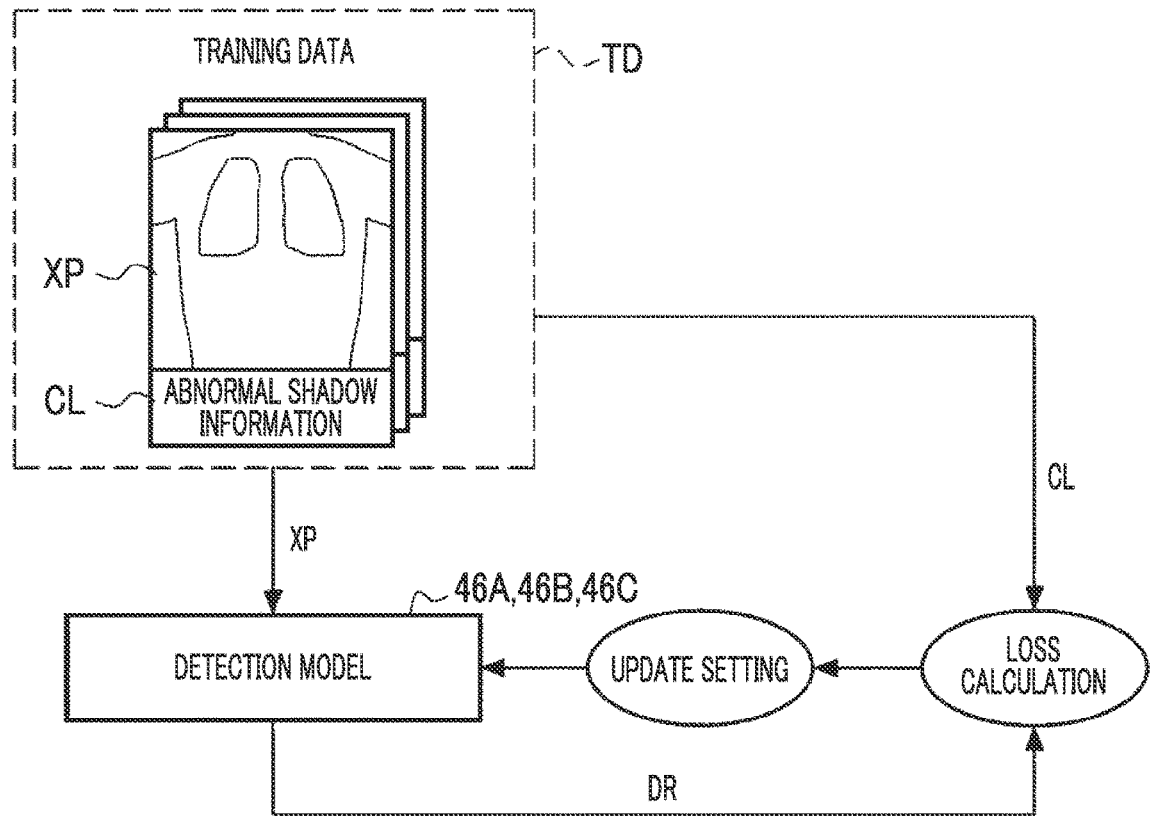
FIG. 7 is a diagram showing an example of processing that is executed in a learning phase where a detection model according to the embodiment of the technique of the disclosure is made to perform learning through machine learning.

FIG. 7 is a diagram showing an example of processing that is executed in a learning phase where the first to third detection models 46A to 46C are made to perform learning through machine learning. Each of the first to third detection models 46A to 46C performs learning using training data TD. The training data TD includes a plurality of radiographic images XP attached with a correct answer label CL. The radiographic images XP included in the training data TD are sample images including various abnormal shadows. The correct answer label CL is, for example, positional information of an abnormal shadow in the radiographic image XP.

In the learning phase, a radiographic image XP is input to each of the first to third detection models 46A to 46C. Each of the first to third detection models 46A to 46C outputs a detection result DR that is a result of detecting an abnormal shadow from the input radiographic image XP. Loss calculation using a loss function is performed based on the detection result DR and the correct answer label CL. Then, update setting of various coefficients (weight coefficient, bias, and the like) of the first to third detection models 46A to 46C is performed depending on a result of the loss calculation, and the first to third detection models 46A to 46C are updated depending on the update setting.

In the learning phase, the series of processing of the input of the radiographic image XP to the first to third detection models 46A to 46C, the output of the detection result DR from the first to third detection models 46A to 46C, the loss calculation, the update setting, and the update of the first to third detection models 46A to 46C is repeatedly executed. The repetition of the series of processing ends in a case where the detection accuracy of an abnormal shadow reaches a predetermined set level in each detection model. Each of the first to third detection models 46A to 46C in which the detection accuracy reaches the set level is stored as a learned detection model in the nonvolatile memory 43. The first to third detection models 46A to 46C are used for the CAD processing that is executed in the diagnosis support unit 40.

In this way, the medical image processing apparatus 10 according to the embodiment has a function of executing the CAD processing accompanied with the image processing on the acquired radiographic image, in addition to a function of capturing the radiographic image. Note that power supply from the battery 50 to the diagnosis support unit 40 including the GPU 41 executing the CAD processing is required, and the amount of power to be consumed from the battery 50 increases compared to a case where the function of the CAD processing is not provided. As a result, it is expected that the operation time of the medical image processing apparatus 10 is shortened or the charging frequency of the battery 50 increases, and efficient rounds may be obstructed.

Accordingly, the medical image processing apparatus 10 according to the embodiment executes the CAD processing with a selected processing method among a plurality of processing methods that are different in amount of power consumption, in a case of executing the CAD processing, thereby suppressing the amount of power to be consumed from the battery 50. Specifically, a detection model for use among the first to third detection models 46A to 46C is selected based on the residual quantity of the battery 50, and the CAD processing is performed using the selected detection model.

Figure 8:
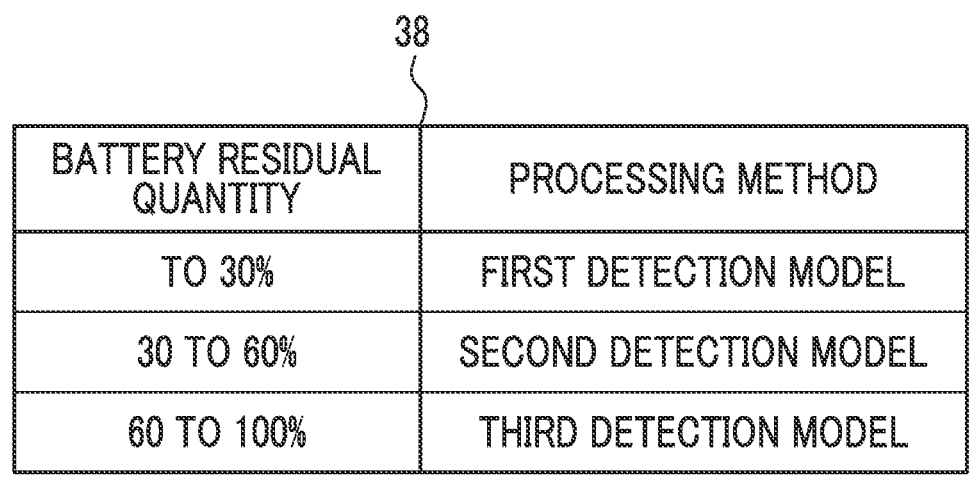
FIG. 8 is a diagram showing an example of a processing method selection table according to the embodiment of the technique of the disclosure.

FIG. 8 is a diagram showing an example of the processing method selection table 38 stored in the nonvolatile memory 33 of the console 30. The processing method selection table 38 is a table in which the residual quantity of the battery 50 is correlated with the detection model for use in the CAD processing. That is, in the processing method selection table 38, the processing method of the CAD processing depending on the residual quantity of the battery 50 is defined. With the processing method selection table 38 illustrated in FIG. 8, in a case where the residual quantity of the battery 50 is less than 30%, the processing method using the first detection model 46A is selected, in a case where the residual quantity of the battery 50 is equal to or greater than 30% and less than 60%, the processing method using the second detection model 46B is selected, and in a case where the residual quantity of the battery 50 is equal to or greater than 60%, the processing method using the third detection model 46C is selected.

Figure 9:
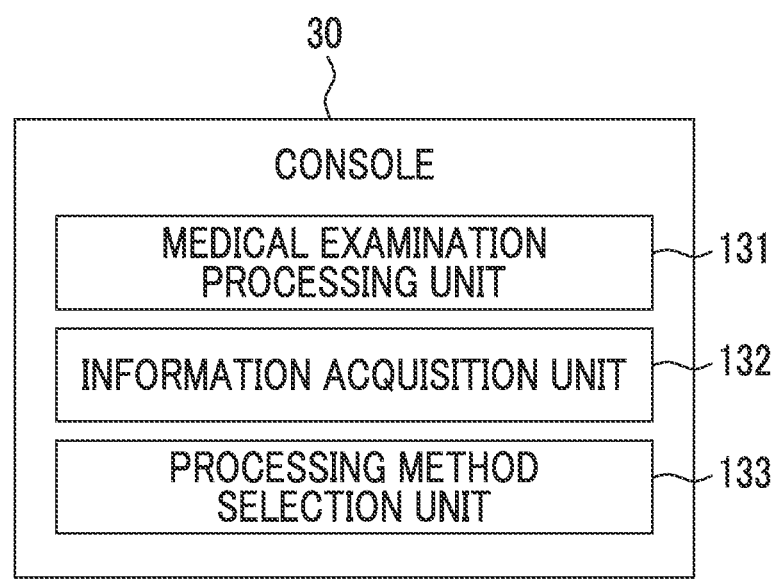
FIG. 9 is a functional block diagram showing an example of the functional configuration of the console according to the embodiment of the technique of the disclosure.

FIG. 9 is a functional block diagram showing an example of the functional configuration of the console 30. The console 30 includes a medical examination processing unit 131, an information acquisition unit 132, and a processing method selection unit 133. The CPU 31 executes the medical examination processing program 37, whereby the console 30 functions as the medical examination processing unit 131, the information acquisition unit 132, and the processing method selection unit 133.

The medical examination processing unit 131 performs setting of irradiation conditions of radiation, acquisition of a radiographic image, an execution instruction of the CAD processing, and acquisition and display of a result of the CAD processing, and the like.

The information acquisition unit 132 acquires information indicating the residual quantity of the battery 50 notified from the battery 50 as information for selecting a processing method of the CAD processing.

The processing method selection unit 133 selects a processing method corresponding to the residual quantity of the battery 50 indicated by information acquired by the information acquisition unit 132 among the processing methods using any one of the first to third detection models 46A to 46C referring to the processing method selection table 38.

Figure 10:
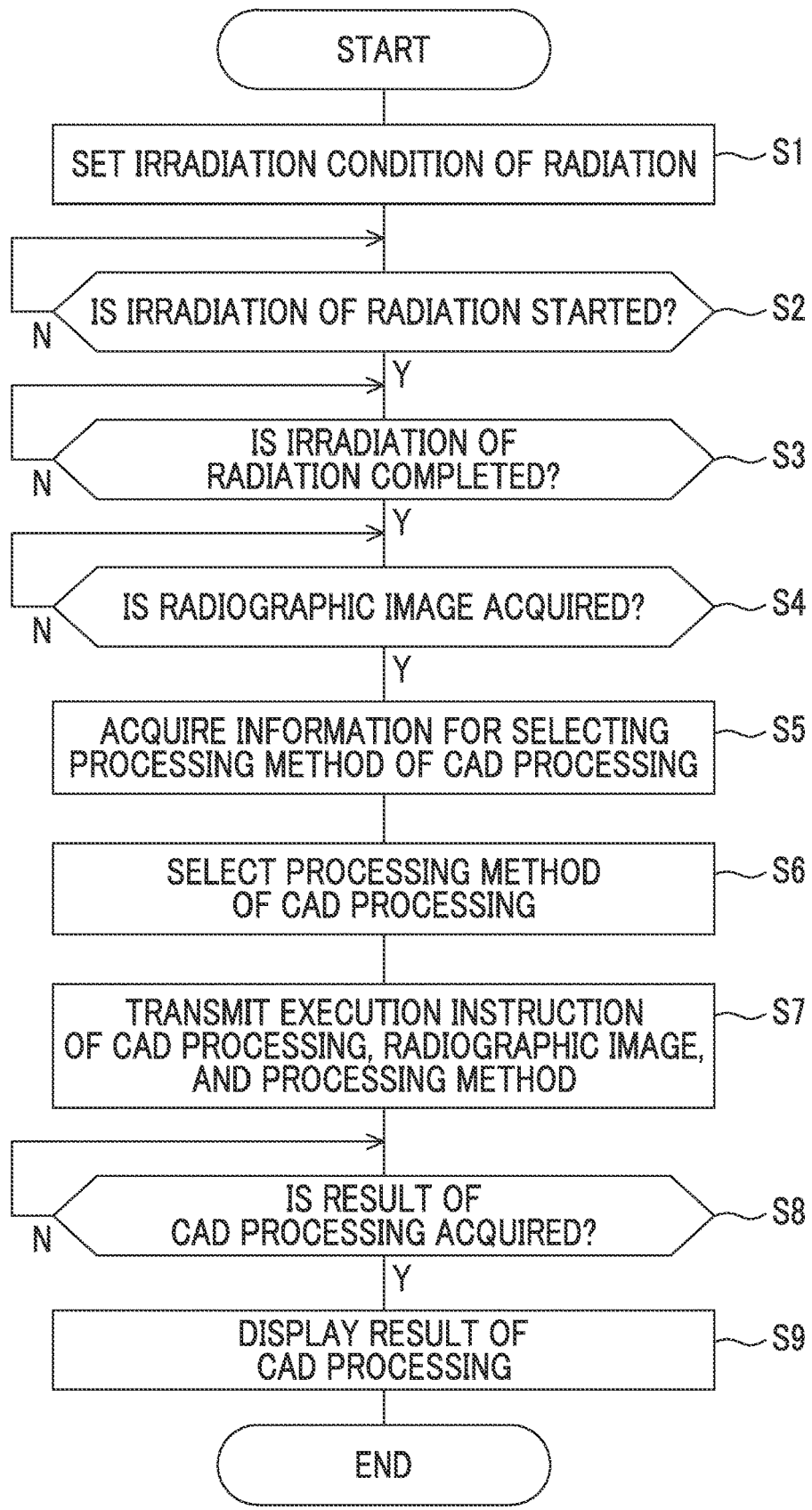
FIG. 10 is a flowchart illustrating an example of a flow of processing that is executed by executing a medical examination processing program according to the embodiment of the technique of the disclosure.

FIG. 10 is a flowchart illustrating an example of a flow of medical examination processing that is executed by the CPU 31 of the console 30 executing the medical examination processing program 37. The medical examination processing program 37 is executed, for example, in a case where the user, such as a radiology technician or a physician, gives an instruction to start the medical examination processing by operating the touch panel display 34.

In Step S1, the CPU 31 functions as the medical examination processing unit 131 and performs processing of setting the irradiation conditions of the radiation from the radiation irradiation unit 20. Specifically, the CPU 31 displays a selection screen of an imaging menu on the touch panel display 34 and receives a selection instruction of an imaging menu. The user, such as a radiology technician or a physician, selects an imaging menu corresponding to an imaging procedure designated in medical examination order information supplied from a radiology information system (RIS) (not shown). The console 30 can be connected to the RIS through the wireless interface 35. The CPU 31 supplies the irradiation conditions of the radiation including a tube voltage, a tube current, and an irradiation time corresponding to the selected imaging menu to the controller 21 of the radiation irradiation unit 20. With this, in the radiation irradiation unit 20, the irradiation conditions of the radiation including the tube voltage, the tube current, and the irradiation time are set. The user can correct the irradiation conditions of the radiation correlated with the imaging menu by operating the touch panel display 34.

In Step S2, the CPU 31 functions as the medical examination processing unit 131 and determines whether or not the irradiation of the radiation is started. The CPU 31 determines that the irradiation of the radiation is started, for example, in a case where detection is made that the irradiation switch 14 is pushed to the second stage.

In Step S3, the CPU 31 functions as the medical examination processing unit 131 and determines whether or not the irradiation of the radiation is completed. The CPU 31 determines that the irradiation of the radiation is completed, for example, in a case where determination is made that the irradiation time set in Step S1 has elapsed from a time at which the irradiation of the radiation is started.

The radiation that is emitted from the radiation irradiation unit 20 and is transmitted through the subject reaches the electronic cassette 60. The electronic cassette 60 detects the radiation transmitted through the subject to generate a radiographic image and transmits the generated radiographic image to the console 30 through wireless communication.

In Step S4, the CPU 31 functions as the medical examination processing unit 131 and determines whether or not the radiographic image transmitted from the electronic cassette 60 is acquired. In a case where determination is made that the radiographic image is acquired, the CPU 31 stores the acquired radiographic image in the nonvolatile memory 33 and transitions the process to Step S5.

In Step S5, the CPU 31 functions as the information acquisition unit 132 and acquires information indicating the residual quantity of the battery 50 notified from the battery 50 as information for selecting a processing method of the CAD processing.

In Step S6, the CPU 31 functions as the processing method selection unit 133 and selects a processing method corresponding to the residual quantity of the battery 50 indicated by information acquired in Step S5 among the processing methods using any one of the first to third detection models 46A to 46C referring to the processing method selection table 38.

In Step S7, the CPU 31 functions as the medical examination processing unit 131 and transmits the execution instruction of the CAD processing, the radiographic image as a CAD processing target, and information (hereinafter, referred to as processing method information) indicating the processing method selected in Step S6 to the diagnosis support unit 40. The CPU 31 may transmit the execution instruction of the CAD processing, the radiographic image as a CAD processing target, and the processing method information to the diagnosis support unit 40 based on an instruction from the user.

In a case where the execution instruction of the CAD processing, the radiographic image as a CAD processing target, and the processing method information are received, the diagnosis support unit 40 executes the CAD processing accompanied with the image processing on the radiographic image as a CAD processing target using a detection model indicated by the processing method information among the first to third detection models 46A to 46C and transmits a result of the CAD processing to the console 30.

In Step S8, the CPU 31 functions as the medical examination processing unit 131 and determines whether or not the result of the CAD processing transmitted from the diagnosis support unit 40 is acquired.

In Step S9, the CPU 31 functions as the medical examination processing unit 131 and displays the result of the CAD processing acquired in Step S8 on the touch panel display 34.

Figure 11:
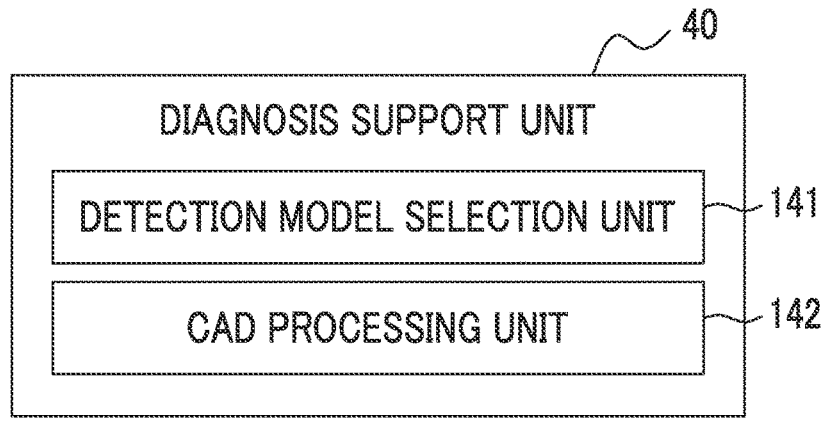
FIG. 11 is a functional block diagram showing an example of the functional configuration of the diagnosis support unit according to the embodiment of the technique of the disclosure.

FIG. 11 is a functional block diagram showing an example of the functional configuration of the diagnosis support unit 40. The diagnosis support unit 40 includes a detection model selection unit 141 and a CAD processing unit 142. The GPU 41 executes the CAD processing program 45, whereby the diagnosis support unit 40 functions as the detection model selection unit 141 and the CAD processing unit 142.

The detection model selection unit 141 selects the detection model indicated by the processing method information transmitted from the console 30 among the first to third detection models 46A to 46C.

The CAD processing unit 142 executes the CAD processing accompanied with the image processing of the radiographic image as a CAD processing target using the detection model selected by the detection model selection unit 141 in response to the execution instruction of the CAD processing transmitted from the console 30. Specifically, the CAD processing unit 142 inputs the radiographic image as a CAD processing target to the detection model selected by the detection model selection unit 141 among the first to third detection models 46A to 46C stored in the nonvolatile memory 43. With this, the detection model detects an abnormal shadow, such as a lesion part, included in the radiographic image as a CAD processing target. The CAD processing unit 142 outputs, for example, positional information indicating a coordinate position in the radiographic image of the abnormal shadow detected by the detection model as the result of the CAD processing. The CAD processing unit 142 may output an image with a mark indicating the position of the abnormal shadow attached to the radiographic image as a CAD processing target as the result of the CAD processing. The CAD processing unit 142 may specify a type of a disease corresponding to the detected abnormal shadow and may include the specified type in the result of the CAD processing. The CAD processing unit 142 transmits the result of the CAD processing to the console 30.

Figure 12:
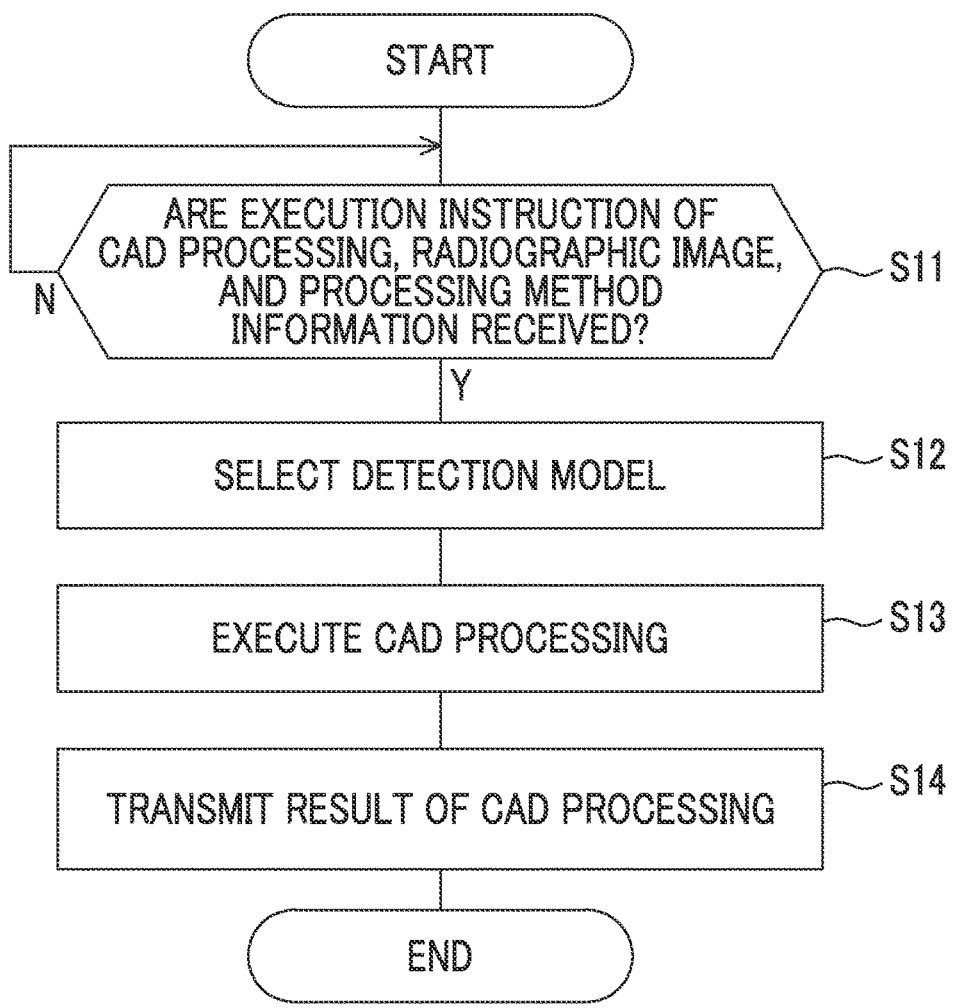
FIG. 12 is a flowchart illustrating a flow of processing that is executed by executing a CAD processing program according to the embodiment of the technique of the disclosure.

FIG. 12 is a flowchart illustrating an example of a flow of processing that is executed by the GPU 41 of the diagnosis support unit 40 executing the CAD processing program 45.

The CAD processing program 45 is executed, for example, accompanied with an execution start of the medical examination processing program 37.

In Step S11, the GPU 41 functions as the CAD processing unit 142 and determines whether or not the execution instruction of the CAD processing, the radiographic image as a CAD processing target, and the processing method information transmitted from the console 30 are received. In a case where determination is made that the execution instruction of the CAD processing, the radiographic image as a CAD processing target, and the processing method information are received, the GPU 41 transitions the process to Step S12.

In Step S12, the GPU 41 functions as the detection model selection unit 141 and selects the detection model indicated by the processing method information received in Step S11 among the first to third detection models 46A to 46C.

In Step S13, the GPU 41 functions as the CAD processing unit 142 and executes the CAD processing accompanied with the image processing on the radiographic image as a CAD processing target received in Step S11 using the detection model selected in Step S12 among the first to third detection models 46A to 46C. In Step S14, the GPU 41 transmits the result of the CAD processing to the console 30.

As described above, with the medical image processing apparatus 10 according to the embodiment of the technique of the disclosure, the GPU 41 of the diagnosis support unit 40 that executes the CAD processing accompanied with the image processing on the medical image executes the CAD processing with the processing method selected based on the residual quantity of the battery 50 among a plurality of processing methods in which the amount of power consumption is different. The selection of the processing method is realized by selecting the detection model for use in the CAD processing among the first to third detection models 46A to 46C.

With the medical image processing apparatus 10, as described above, for example, in a case where the residual quantity of the battery 50 is small, control can be performed such that the CAD processing is executed using the detection model where the amount of power consumption is relatively small. With this, it is possible to suppress the amount of power consumption in the diagnosis support unit 40 (GPU 41), and to suppress the amount of power to be consumed from the battery 50. Accordingly, it is possible to extend the operation time of the medical image processing apparatus 10. It is also possible to decrease the charging frequency of the battery 50. Therefore, it is possible to perform efficient rounds using the medical image processing apparatus 10.

Second Embodiment

The medical image processing apparatus 10 according to the first embodiment described above selects the processing method of the CAD processing based on information indicating the residual quantity of the battery 50. In contrast, a medical image processing apparatus 10 according to a second embodiment selects the processing method of the CAD processing based on information indicating a purpose of the CAD processing. The purpose of the CAD processing is a purpose of a medical examination that is performed using the medical image processing apparatus 10, and examples of the purpose include progress observation, precise diagnosis, and cause analysis.

FIG. 13 is a diagram showing an example of a processing method selection table 38A according to the embodiment.

The processing method selection table 38A is a table in which the purpose of the CAD processing is correlated with the detection model for use in the CAD processing. That is, tin the processing method selection table 38A, the processing method of the CAD processing depending on the purpose of the CAD processing is defined. With the processing method selection table 38, in a case where the purpose of the CAD processing is the progress observation, the processing method using the first detection model 46A is selected, in a case where the purpose of the CAD processing is the precise diagnosis, the processing method using the second detection model 46B is selected, and in a case where the purpose of the CAD processing is the cause analysis, the processing method using the third detection model 46C is selected.

In a case where the purpose of the CAD processing is the progress observation, since a known abnormal shadow is detected from the radiographic image, it is considered that the detection of the abnormal shadow with high accuracy is not required. Accordingly, in a case where the purpose of the CAD processing is the progress observation, it is considered that it is possible to execute the CAD processing using the first detection model 46A where the detection accuracy of the abnormal shadow is relatively low. On the other hand, in a case where the purpose of the CAD processing is the precise diagnosis or the cause analysis, it is preferable that the abnormal shadow is detected with high accuracy, and in particular, in a case where the purpose of the CAD processing is the cause analysis, it is preferable that the abnormal shadow is detected with the highest accuracy. Accordingly, it is preferable that, in a case where the purpose of the CAD processing is the precise diagnosis, the CAD processing is executed using the second detection model 46B where the detection accuracy of the abnormal shadow is relatively high, and in a case where the purpose of the CAD processing is the cause analysis, the CAD processing is executed using the third detection model 46C where the detection accuracy of the abnormal shadow is the highest.

In the embodiment, the information acquisition unit 132 (see FIG. 9) that is a functional unit of the console 30 acquires information indicating the purpose of the CAD processing as information for selecting the processing method of the CAD processing. Information indicating the purpose of the CAD processing may be input by the user operating the touch panel display 34, for example, in a case of capturing the radiographic image. In a case where information indicating the purpose of the CAD processing is included in the medical examination order information supplied from the RIS, the information acquisition unit 132 may acquire information indicating the purpose of the CAD processing by acquiring the medical examination order information.

In the embodiment, the processing method selection unit 133 (see FIG. 9) that is a functional unit of the console 30 selects the processing method corresponding to the purpose of the CAD processing indicated by information acquired by the information acquisition unit 132 among the processing methods using any one of the first to third detection models 46A to 46C referring to the processing method selection table 38A.

In the embodiment, in Step S5 of the flowchart shown in FIG. 10, the CPU 31 of the console 30 functions as the information acquisition unit 132 and acquires information indicating the purpose of the CAD processing as information for selecting the processing method of the CAD processing. In regard to information indicating the purpose of the CAD processing, for example, information input by a user's operation on the touch panel display 34 or may be acquired by acquiring the medical examination order supplied from the RIS.

In Step S6, the CPU 31 functions as the processing method selection unit 133 and selects the processing method corresponding to the purpose of the CAD processing indicated by information acquired in Step S5 among the processing methods using any one of the first to third detection models 46A to 46C referring to the processing method selection table 38A.

With the medical image processing apparatus 10 according to the embodiment, as described above, for example, in a case where the purpose of the CAD processing does not require the detection of the abnormal shadow with high accuracy, control can be performed such that the CAD processing is executed using the detection model where the amount of power consumption is relatively small. With this, it is possible to suppress the amount of power consumption in the diagnosis support unit 40 (GPU 41), and to suppress the amount of power to be consumed from the battery 50.

Third Embodiment

The medical image processing apparatus 10 according to the first embodiment described above selects the processing method of the CAD processing based on information indicating the residual quantity of the battery 50, and the medical image processing apparatus 10 according to the second embodiment selects the processing method of the CAD processing based on information indicating the purpose of the CAD processing. In contrast, a medical image processing apparatus 10 according to a third embodiment selects the processing method of the CAD processing based on both information indicating the residual quantity of the battery 50 and information indicating the purpose of the CAD processing.

FIG. 14 is a diagram showing an example of a processing method selection table 38B according to the embodiment. The processing method selection table 38B is a table in which a combination of the purpose of the CAD processing and the residual quantity of the battery 50 is correlated with the detection model for use in the CAD processing. That is, in the processing method selection table 38B, the processing method of the CAD processing depending on the combination of the purpose of the CAD processing and the residual quantity of the battery 50 is defined. With the processing method selection table 38B, for example, in a case where the purpose of the CAD processing is the progress observation and the residual quantity of the battery 50 is less than 30%, the processing method using the first detection model 46A is selected, in a case where the purpose of the CAD processing is the precise diagnosis and the battery residual quantity is equal to or greater than 30% and less than 60%, the processing method using the second detection model 46B is selected, and in a case where the purpose of the CAD processing is the cause analysis and the residual quantity of the battery 50 is equal to or greater than 60% and less than 100%, the processing method using the third detection model 46C is selected.

In the embodiment, the information acquisition unit 132 (see FIG. 9) that is a functional unit of the console 30 acquires information indicating the purpose of the CAD processing and information indicating the residual quantity of the battery 50 as information for selecting the processing method of the CAD processing.

In the embodiment, the processing method selection unit 133 (see FIG. 9) that is a functional unit of the console 30 selects the processing method corresponding to the combination of the purpose of the CAD processing and the residual quantity of the battery 50 indicated by information acquired by the information acquisition unit 132 among the processing methods using any one of the first to third detection models 46A to 46C referring to the processing method selection table 38B.

In the embodiment, in Step S5 of the flowchart shown in FIG. 10, the CPU 31 of the console 30 functions as the information acquisition unit 132 and acquires information indicating the purpose of the CAD processing and information indicating the residual quantity of the battery 50 as information for selecting the processing method of the CAD processing.

In Step S6, the CPU 31 functions as the processing method selection unit 133 and selects the processing method corresponding to the combination of the purpose of the CAD processing and the residual quantity of the battery 50 indicated by information acquired in Step S5 among the processing methods using any one of the first to third detection models 46A to 46C referring to the processing method selection table 38B.

With the medical image processing apparatus 10 according to the embodiment, for example, as described above, in a case where the purpose of the CAD processing does not require the detection of the abnormal shadow with high accuracy and the residual quantity of the battery 50 is small, control can be performed such that the CAD processing is executed using the detection model where the amount of power consumption is relatively small. With this, it is possible to suppress the amount of power consumption in the diagnosis support unit 40 (GPU 41), and to suppress the amount of power to be consumed from the battery 50.

Fourth Embodiment

The medical image processing apparatus 10 according to the first embodiment described above selects the processing method of the CAD processing based on information indicating the residual quantity of the battery 50. In contrast, a medical image processing apparatus 10 according to a fourth embodiment selects any one of a plurality of processing methods based on information indicating an execution schedule of the CAD processing. The execution schedule of the CAD processing is a schedule of a medical examination that is performed using the medical image processing apparatus 10. Information indicating the execution schedule of the CAD processing is included in, for example, the medical examination order information supplied from the RIS.

Figures 15, 16:
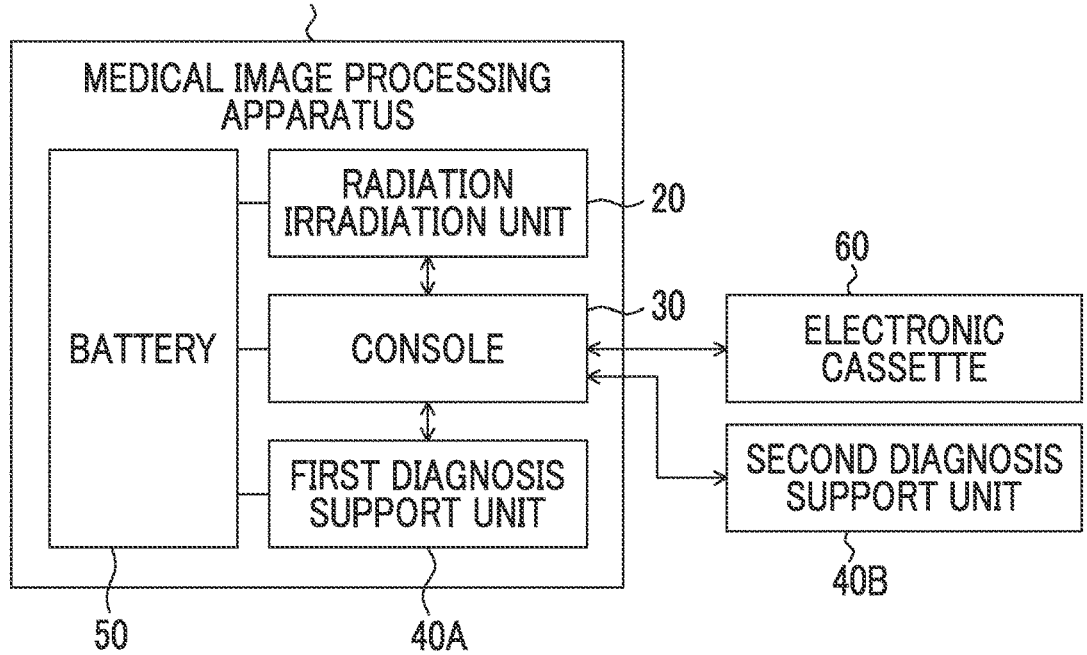
FIG. 15 is a diagram showing an example of medical examination order information according to another embodiment of the technique of the disclosure.
FIG. 16 is a block diagram showing an example of the configuration of a medical examination system according to another embodiment of the technique of the disclosure.

FIG. 15 is a diagram showing an example of medical examination order information 400. In the medical examination order information 400, for example, an order number, a patient ID, an imaging procedure, and a medical examination purpose are included. The medical examination order information 400 is issued for each medical examination date on a plurality of patients to be a target of a medical examination using the medical image processing apparatus 10. That is, information indicating the execution schedule of the CAD processing in a day is included in the medical examination order information 400.

In the embodiment, the information acquisition unit 132 (see FIG. 9) that is a functional unit of the console 30 acquires information indicating the execution schedule of the CAD processing, that is, the medical examination order information as information for selecting the processing method of the CAD processing.

In the embodiment, the processing method selection unit 133 (see FIG. 9) that is a functional unit of the console 30 selects one processing method among the processing methods using any one of the first to third detection models 46A to 46C based on information (medical examination order information) indicating the execution schedule of the CAD processing. The processing method selection unit 133 specifies the number of patients (that is, the scheduled number of times of the CAD processing) to be a medical examination target included in the medical examination order information. The processing method selection unit 133 may select the processing method using the third detection model 46C on all patients in a case where the number n of patients to be a medical examination target is less than a first threshold value TH1 (n<TH1). In a case where the number n of patients to be a medical examination target is equal to or greater than the first threshold value TH1 and less than a second threshold value TH2 (TH1≤n<TH2), the processing method selection unit 133 may select the processing method using the first detection model 46A on a patient who has a medical examination (CAD processing) for the progress observation and may select the processing method using the third detection model 46C on a patient who has a medical examination (CAD processing) for the precise diagnosis and the cause analysis. In a case where the number n of patients to be a medical examination target is equal to or greater than the second threshold value TH2 (n≥TH2), the processing method selection unit 133 may select the processing method using the first detection model 46A on a patient who has a medical examination (CAD processing) for the progress observation, may select the processing method using the second detection model 46B on a patient who has a medical examination (CAD processing) for the precise diagnosis, and may select the processing method using the third detection model 46C on a patient who has a medical examination (CAD processing) for the cause analysis.

In the embodiment, in Step S5 of the flowchart shown in FIG. 10, the CPU 31 of the console 30 functions as the information acquisition unit 132 and acquires information indicating the execution schedule of the CAD processing, that is, the medical examination order information as information for selecting the processing method of the CAD processing. The medical examination order information is supplied from the RIS that is connected to the console 30 through the wireless interface 35. The medical examination order information may be downloaded to the nonvolatile memory 33 in advance before rounds on the medical examination date.

In Step S6, the CPU 31 functions as the processing method selection unit 133 and selects one processing method among the processing methods using any one of the first to third detection models 46A to 46C based on information indicating the execution schedule of the CAD processing acquired in Step S5.

With the medical image processing apparatus 10 according to the embodiment, as described above, for example, in a case where the scheduled number of times of the CAD processing (the number of patients to be a medical examination target) specified based on information (medical examination order information) indicating the execution schedule of the CAD processing is greater than a threshold value, control can be performed such that the CAD processing is executed using the detection model where the amount of power consumption is relatively small, depending on the purpose of the diagnosis. With this, it is possible to suppress the amount of power consumption in the diagnosis support unit 40 (GPU 41), and to suppress the amount of power to be consumed from the battery 50.

Fifth Embodiment

FIG. 16 is a diagram showing an example of the configuration of a medical examination system 1 according to a fifth embodiment of the technique of the disclosure. The medical examination system 1 according to the embodiment comprises, as a diagnosis support unit that executes the CAD processing, a first diagnosis support unit 40A that is provided inside the medical image processing apparatus 10, and a second diagnosis support unit 40B that is provided outside the medical image processing apparatus 10. The first diagnosis support unit 40A corresponds to the diagnosis support unit 40 according to the first to fourth embodiments described above.

Figures 17, 18:
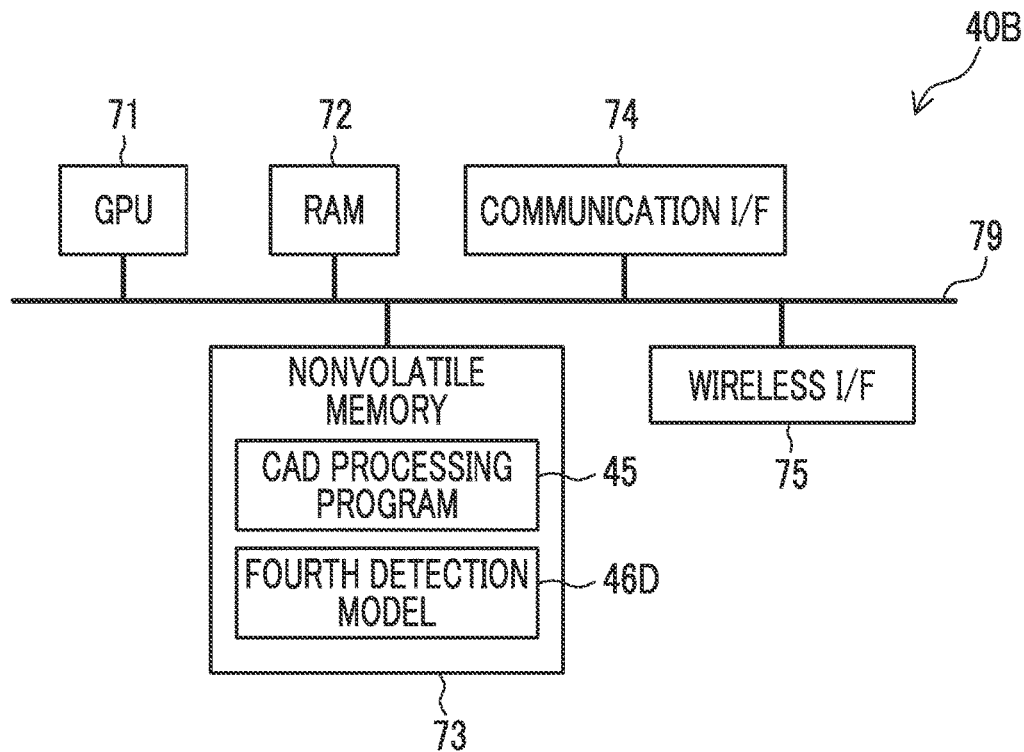
FIG. 17 is a diagram showing an example of the hardware configuration of a second diagnosis support unit according to the embodiment of the technique of the disclosure.
FIG. 18 is a diagram showing an example of a processing method selection table according to another embodiment of the technique of the disclosure.

FIG. 17 is a diagram showing an example of the hardware configuration of the second diagnosis support unit 40B. The second diagnosis support unit 40B has the substantially same hardware configuration as the first diagnosis support unit 40A, and has a GPU 71, a RAM 72, a nonvolatile memory 73, a communication interface 74, and a wireless interface 75. The GPU 71, the RAM 72, the nonvolatile memory 73, the communication interface 74, and the wireless interface 75 are connected to the bus 79. The GPU 71 is an example of a third processor in the technique of the disclosure. The second diagnosis support unit 40B is provided at a place different from the medical image processing apparatus 10, and can perform communication with the console 30 by wireless communication through the wireless interface 75. The second diagnosis support unit 40B receives supply of power from a power supply (not shown) different from the battery 50 in the medical image processing apparatus 10.

The nonvolatile memory 73 stores a CAD processing program 45 and a fourth detection model 46D. The CAD processing program 45 is the same as that stored in a nonvolatile memory 43 of the first diagnosis support unit 40A. The fourth detection model 46D may be the same as any one of the first to third detection models 46A to 46C stored in the nonvolatile memory 43 of the first diagnosis support unit 40A. Typically, the fourth detection model 46D is the same as the third detection model 46C where the detection accuracy of the abnormal shadow is the highest.

The second diagnosis support unit 40B executes the CAD processing using the fourth detection model 46D and transmits the result of the CAD processing to the console 30 in response to an instruction from the console 30. The second diagnosis support unit 40B is made to execute the CAD processing, whereby the medical image processing apparatus 10 can obtain the result of the CAD processing with no consumption of power from the battery 50.

In the medical image processing apparatus 10 according to the embodiment, in a case of executing the CAD processing, any one of the processing method using any one of the first to third detection models 46A to 46C by the first diagnosis support unit 40A (GPU 41) or the processing method using the fourth detection model 46D by the second diagnosis support unit 40B (GPU 71) is selected, and the CAD processing is executed by the selected processing method.

FIG. 18 is a diagram showing an example of a processing method selection table 38C according to the embodiment. The processing method selection table 38C is a table in which the residual quantity of the battery 50 is correlated with the diagnosis support unit and the detection model for use in the CAD processing. That is, in the processing method selection table 38C, the processing method of the CAD processing depending on the residual quantity of the battery 50 is defined. With the processing method selection table 38C illustrated in FIG. 18, in a case where the residual quantity of the battery 50 is less than 10%, the processing method using the fourth detection model 46D by the second diagnosis support unit 40B is selected. In this case, there is no consumption of power from the battery 50. In a case where the residual quantity of the battery 50 is equal to or greater than 10% and less than 30%, the processing method using the first detection model 46A by the first diagnosis support unit 40A is selected, in a case where the residual quantity of the battery 50 is equal to or greater than 30% and less than 60%, the processing method using the second detection model 46B by the first diagnosis support unit 40A is selected, and in a case where the residual quantity of the battery 50 is equal to or greater than 60%, the processing method using the third detection model 46C by the first diagnosis support unit 40A is selected.

In the embodiment, the information acquisition unit 132 (see FIG. 9) that is a functional unit of the console 30 acquires information indicating the residual quantity of the battery 50 as information for selecting the processing method of the CAD processing.

In the embodiment, the processing method selection unit 133 (see FIG. 9) that is a functional unit of the console 30 selects the processing method corresponding to the residual quantity of the battery 50 indicated by information acquired by the information acquisition unit 132 among the processing methods using any one of the first to third detection models 46A to 46C by the first diagnosis support unit 40A and the processing method using the fourth detection model 46D by the second diagnosis support unit 40B referring to the processing method selection table 38C.

In the embodiment, in Step S5 of the flowchart shown in FIG. 10, the CPU 31 of the console 30 functions as the information acquisition unit 132 and acquires information indicating the residual quantity of the battery 50 as information for selecting the processing method of the CAD processing.

In Step S6, the CPU 31 functions as the processing method selection unit 133 and selects the processing method corresponding to the residual quantity of the battery 50 indicated by information acquired in Step S5 among the processing methods using any one of the first to fourth detection models 46A to 46D referring to the processing method selection table 38C.

In Step S7, the CPU 31 functions as the medical examination processing unit 131 and transmits the execution instruction of the CAD processing, the radiographic image as a CAD processing target, and the processing method information to one diagnosis support unit corresponding to the processing method selected in Step S6 between the first diagnosis support unit 40A and the second diagnosis support unit 40B.

In a case where the execution instruction of the CAD processing, the radiographic image as a CAD processing target, and the processing method information are received, the first diagnosis support unit 40A or the second diagnosis support unit 40B executes the CAD processing on the radiographic image as a CAD processing target using the detection model indicated by the processing method information and transmits the result of the CAD processing to the console 30.

With the medical image processing apparatus 10 according to the embodiment, as described above, for example, in a case where the residual quantity of the battery 50 is less than a threshold value, control can be performed such that CAD processing is executed using the second diagnosis support unit 40 (GPU 71). With this, it is possible to suppress the amount of power consumption in the first diagnosis support unit 40 (GPU 41), and to suppress the amount of power to be consumed from the battery 50.

Figure 19:
FIG. 19 is a diagram showing an example of a processing method selection table according to another embodiment of the technique of the disclosure.

In a case where the medical examination system 1 comprises the second diagnosis support unit 40B, any one of a plurality of processing methods may be selected based on both the residual quantity of the battery 50 and information indicating the purpose of the CAD processing. FIG. 19 is a diagram showing an example of a processing method selection table 38D according to a modification example. The processing method selection table 38D is a table in which a combination of the purpose of the CAD processing and the residual quantity of the battery 50 is correlated with the diagnosis support unit and the detection model for use in the CAD processing. That is, in the processing method selection table 38D, the processing method of the CAD processing depending on the combination of the purpose of the CAD processing and the residual quantity of the battery 50 is defined.

With the processing method selection table 38D, in a case where the purpose of the CAD processing is the progress observation, any one of the processing method using the fourth detection model 46D by the second diagnosis support unit 40B or the processing method using the first detection model 46A or the processing method using the second detection model 46B by the first diagnosis support unit 40A is selected on the residual quantity of the battery 50. In a case where the purpose of the CAD processing is the precise diagnosis, any one of the processing method using the fourth detection model 46D by the second diagnosis support unit 40B or the processing method using the second detection model 46B or the processing method using the third detection model 46C by the first diagnosis support unit 40A is selected depending on the residual quantity of the battery 50. In a case where the purpose of the CAD processing is the cause analysis, any one of the processing method using the fourth detection model 46D by the second diagnosis support unit 40B or the processing method using the third detection model 46C by the first diagnosis support unit 40A is selected depending on the residual quantity of the battery 50.

Sixth Embodiment

In the medical image processing apparatus 10 according to the first to fifth embodiments described above, a plurality of processing methods that are selectively used in the CAD processing are different in calculation processing amount. Specifically, the CAD processing is executed selectively using the first to third detection models 46A to 46C that are different in calculation processing amount. In contrast, in a medical image processing apparatus 10 according to the embodiment, a plurality of processing methods that are selectively used in the CAD processing are different in the number of pixels (resolution) of a radiographic image as a target of the CAD processing. Accordingly, a plurality of processing methods are different in amount of power consumption.

FIG. 20 is a diagram showing an example of the hardware configuration of a diagnosis support unit 40 according to the embodiment. The diagnosis support unit 40 according to the embodiment executes the CAD processing using a single detection model 46.

FIG. 21 is a functional block diagram showing an example of the functional configuration of the diagnosis support unit 40 according to the embodiment. The diagnosis support unit 40 has a resolution conversion unit 143 and a CAD processing unit 142. The GPU 41 executes the CAD processing program 45, whereby the diagnosis support unit 40 functions as the resolution conversion unit 143 and the CAD processing unit 142.

The resolution conversion unit 143 executes resolution conversion processing on the radiographic image as a CAD processing target to have a resolution indicated by the processing method information transmitted from the console 30. Specifically, in a case where the resolution indicated by the processing method information transmitted from the console 30 is a low resolution, the resolution conversion unit 143 executes resolution conversion processing of reducing the number of pixels, for example, by 40% on the radiographic image as a CAD processing target, thereby decreasing the resolution of the radiographic image as a CAD processing target. In a case where the resolution indicated by the processing method information transmitted from the console 30 is a middle resolution, the resolution conversion unit 143 executes resolution conversion processing of reducing the number of pixels, for example, by 20% on the radiographic image as a CAD processing target, thereby decreasing the resolution of the radiographic image as a CAD processing target. In a case where the resolution indicated by the processing method information transmitted from the console 30 is a high resolution, the resolution conversion unit 143 does not execute resolution conversion processing on the radiographic image as a CAD processing target and maintains the original resolution.

The CAD processing unit 142 executes the CAD processing in response to the execution instruction of the CAD processing transmitted from the console 30. Specifically, the CAD processing unit 142 inputs the radiographic image where the number of pixels is reduced by the resolution conversion unit 143 or the radiographic image where the number of pixels is not reduced and the resolution is maintained, to the detection model 46. With this, the detection model detects an abnormal shadow, such as a lesion part, included in the radiographic image as a CAD processing target. As the resolution of the radiographic image as a target of the CAD processing is lower, the number of pixels is smaller, and the amount of power consumption in the diagnosis support unit 40 (GPU 41) is smaller. The CAD processing unit 142 transmits the result of the CAD processing to the console 30.

FIG. 22 is a diagram showing an example of a processing method selection table 38E according to the embodiment. The processing method selection table 38E is a table in which the residual quantity of the battery 50 is correlated with the resolution of the radiographic image as a target of the CAD processing. That is, in the processing method selection table 38E, the processing method of the CAD processing depending on the residual quantity of the battery 50 is defined. With the processing method selection table 38E, in a case where the residual quantity of the battery 50 is less than 30%, a processing method that has a radiographic image having a low resolution (the number of pixels is small) as a target of the CAD processing is selected, in a case where the residual quantity of the battery 50 is greater than 30% and less than 60%, a processing method that has a radiographic image having a middle resolution (the number of pixels is middle) as a target of the CAD processing is selected, and in a case where the residual quantity of the battery 50 is greater than 60%, a processing method that has a radiographic image having a high resolution (the number of pixels is large) as a target of the CAD processing is selected.

In the embodiment, the information acquisition unit 132 (see FIG. 9) that is a functional unit of the console 30 acquires information indicating the residual quantity of the battery 50 as information for selecting the processing method of the CAD processing.

In the embodiment, the processing method selection unit 133 (see FIG. 9) that is a functional unit of the console 30 selects the processing method corresponding to the residual quantity of the battery 50 indicated by information acquired by the information acquisition unit 132 among a plurality of processing methods that are different in resolution (the number of pixels) of the radiographic image as a target of the CAD processing, depending on the processing method selection table 38E.

In the embodiment, in Step S5 of the flowchart shown in FIG. 10, the CPU 31 of the console 30 functions as the information acquisition unit 132 and acquires information indicating the residual quantity of the battery 50 as information for selecting the processing method of the CAD processing.

In Step S6, the CPU 31 functions as the processing method selection unit 133 and selects the processing method corresponding to the residual quantity of the battery 50 indicated by information acquired in Step S5 among a plurality of processing methods that are different in resolution (the number of pixels) of the radiographic image as a target of the CAD processing, referring to the processing method selection table 38E.

In Step S7, the CPU 31 functions as the medical examination processing unit 131 and transmits the execution instruction of the CAD processing, the radiographic image as a CAD processing target, and the processing method information indicating the processing method selected in Step S6 to the diagnosis support unit 40.

FIG. 23 is a flowchart showing an example of a flow of processing that is executed by the GPU 41 of the diagnosis support unit 40 executing by executing the CAD processing program 45.

In Step S11, the GPU 41 functions as the CAD processing unit 142 and determines whether or not the execution instruction of the CAD processing, the radiographic image as a CAD processing target, and the processing method information transmitted from the console 30 are received. In a case where determination is made that the execution instruction of the CAD processing, the radiographic image as a CAD processing target, and the processing method information are received, the GPU 41 transitions the process to Step S12A.

In Step S12A, the GPU 41 functions as the resolution conversion unit 143 and executes the resolution conversion processing on the radiographic image as a CAD processing target to have a resolution indicated by the processing method information.

In Step S13, the GPU 41 functions as the CAD processing unit 142 and executes the CAD processing accompanied with the image processing on the radiographic image where the number of pixels is reduced by the resolution conversion processing in Step S12A or the radiographic image where the number of pixels is not reduced and the resolution is maintained. In Step S14, the GPU 41 transmits the result of the CAD processing to the console 30.

As described above, a plurality of processing methods that are selectively used in the CAD processing to be executed in the diagnosis support unit 40 of the medical image processing apparatus 10 according to the embodiment are different in the number of pixels (resolution) of the radiographic image as a target of the CAD processing. With the medical image processing apparatus 10 according to the embodiment, as described above, for example, in a case where the residual quantity of the battery 50 is small, control can be performed such that a radiographic image having a low resolution (the number of pixels is small) is set as a target of the CAD processing. With this, it is possible to suppress the amount of power consumption in the diagnosis support unit 40 (GPU 41), and to suppress the amount of power to be consumed from the battery 50.

The medical image processing apparatus 10 according to the embodiment, it is possible to make modifications following the examples of the second to fifth embodiments described above. That is, the selection of the processing method of the CAD processing may be performed based on information indicating the purpose of the CAD processing or may be performed based on both information indicating the purpose of the CAD processing and information indicating the residual quantity of the battery 50. The selection of the processing method of the CAD processing may be performed based on information indicating the execution schedule of the CAD processing. The CAD processing by the second diagnosis support unit 40B provided outside the medical image processing apparatus 10 may be added to options.

A plurality of processing methods that are selectively used in the CAD processing may be different in both the number of pixels (resolution) of a radiographic image as a target of the CAD processing and calculation processing amount.

In the first to sixth embodiments described above, although a form in which power is supplied to both the console 30 (CPU 31) and the diagnosis support unit 40 (GPU 41) using the single battery 50 has been illustrated, the technique of the disclosure is not limited to the form. For example, as shown in FIG. 24, a medical image processing apparatus 10 may include a first battery 50A that supplies power to the radiation irradiation unit 20 and the console 30 (CPU 31), and a second battery 50B that supplies power to the diagnosis support unit 40 (GPU 41).

In the first to sixth embodiments described above, although a case where the radiographic image is applied as the medical image has been illustrated, the medical image may be, for example, an image, such as an ultrasound image or a magnetic resonance imaging (MRI) image, other than the radiographic image.

In the first to sixth embodiments described above, although a case where the processing of detecting an abnormal shadow included in the medical image has been illustrated as the CAD processing that is executed by the diagnosis support unit 40 (GPU 41), the technique of the disclosure is not limited to the form. The CAD processing accompanied with the image processing may be, for example, processing of enhancing or attenuating a specific part included in the medical image or may be processing of visualizing change of a specific lesion from past images.

In each embodiment described above, for example, as the hardware structures of processing units that executes various kinds of processing, such as the medical examination processing unit 131, the information acquisition unit 132, the processing method selection unit 133, the detection model selection unit 141, and the CAD processing unit 142, various processors described below can be used. Various processors includes a programmable logic device (PLD) that is a processor capable of changing a circuit configuration after manufacture, such as an FPGA, a dedicated electric circuit that is a processor having a circuit configuration dedicatedly designed for executing specific processing, such as an application specific integrated circuit (ASIC), and the like, in addition to a CPU and a GPU that is a general-purpose processor executing software (program) to function as various processing units, as described above.

One processing unit may be configured of one of various processors described above or may be configured of a combination of two or more processors (for example, a combination of a plurality of FPGAs or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Second, as represented by System on Chip (SoC) or the like, there is a form in which a processor that realizes all functions of a system including a plurality of processing units into one integrated circuit (IC) chip is used. In this way, various processing units may be configured using one or more processors among various processors described above as a hardware structure.

In addition, as the hardware structure of various processors is, more specifically, an electric circuit (circuitry), in which circuit elements, such as semiconductor elements, are combined can be used.

In the above-described embodiments, although an aspect where the medical examination processing program 37 is stored in (installed on) the nonvolatile memory 33 in advance, and the CAD processing program 45 is stored in (installed on) the nonvolatile memory 43 in advance has been described, the technique of the disclosure is not limited thereto. Each program described above may be provided in a form of being recorded on a recording medium, such as a compact disc read only memory (CD-ROM), a digital versatile disc read only memory (DVD-ROM), or a universal serial bus (USB) memory. Each program described above may be provided in a form of being downloaded from an external apparatus through a network.

EXPLANATION OF REFERENCES 1 medical examination system
10 medical image processing apparatus
11 wheels
12 arm part
13 shaft part
14 irradiation switch
15 housing portion
20 radiation irradiation unit
21 controller
22 voltage generation unit
23 radiation tube
24 irradiation field limiter
30 console
31 CPU
32 RAM
33 nonvolatile memory
34 touch panel display
35 wireless interface
36 communication interface
37 medical examination processing program
38, 38A to 38E processing method selection table
39 bus
40 diagnosis support unit
40A first diagnosis support unit
40B second diagnosis support unit
41 GPU
42 RAM
43 nonvolatile memory
44 communication interface
45 CAD processing program
46 detection model
46A first detection model
46B second detection model
46C third detection model
46D fourth detection model
49 bus
50 battery
50A first battery
50B second battery
60 electronic cassette
71 GPU
72 RAM
73 nonvolatile memory
74 communication interface
75 wireless interface
79 bus
131 medical examination processing unit
132 information acquisition unit
133 processing method selection unit
141 detection model selection unit
142 CAD processing unit
143 resolution conversion unit
200 user
201 subject
300 examination table
400 medical examination order information
CL correct answer label
DR detection result
R radiation
TD training data
XP radiographic image

What is claimed is:

1. A medical image processing apparatus comprising:
a first processor;
a second processor that executes image processing on a medical image in response to an instruction from the first processor; and
a battery that supplies power to the first processor and the second processor,
wherein the second processor executes the image processing with a selected processing method among a plurality of processing methods that are different in amount of power consumption.

2. The medical image processing apparatus according to claim 1,
wherein the first processor selects any one of the plurality of processing methods based on a residual quantity of the battery.

3. The medical image processing apparatus according to claim 1,
wherein the first processor selects any one of the plurality of processing methods based on information indicating a purpose of the image processing.

4. The medical image processing apparatus according to claim 1,
wherein the first processor selects any one of the plurality of processing methods based on information indicating an execution schedule of the image processing.

5. The medical image processing apparatus according to claim 1,
wherein the plurality of processing methods are different in calculation processing amount.

6. The medical image processing apparatus according to claim 1,
wherein the plurality of processing methods are different in the number of pixels of a medical image to be processed.

7. The medical image processing apparatus according to claim 1,
wherein, in a case where a third processor that receives supply of power from a power supply different from the battery to execute image processing is available,
the first processor selects any one of the plurality of processing methods of the second processor or a processing method of the third processor.

8. The medical image processing apparatus according to claim 7,
wherein the first processor selects the processing method of the third processor in a case where a residual quantity of the battery is equal to or less than a threshold value.

9. The medical image processing apparatus according to claim 1,
wherein the medical image is a radiographic image, and the medical image processing apparatus further comprises:
a radiation irradiation unit that receives the supply of power from the battery to perform irradiation of radiation for capturing the radiographic image.

10. The medical image processing apparatus according to claim 1,
wherein the second processor outputs information for supporting diagnosis using the medical image through the image processing.

11. The medical image processing apparatus according to claim 1,
wherein a first battery that supplies power to the first processor and a second battery that supplies power to the second processor are provided.

12. The medical image processing apparatus according to claim 1,
wherein the medical image processing apparatus is a mobile type.

* * * * *